United States Patent
Peron et al.

(10) Patent No.: US 10,613,070 B2
(45) Date of Patent: Apr. 7, 2020

(54) REFUSAL-BASED METHODS OF ESTABLISHING A CAT OR DOG FOOD PREFERENCE

(71) Applicant: MARS, INCORPORATED, McLean, VA (US)

(72) Inventors: Franck Peron, Lincoln (GB); Oliver Henry Piers Burman, Lincoln (GB); Daniel Simon Mills, Lincoln (GB); Matthew Williams, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 188 days.

(21) Appl. No.: 15/515,706

(22) PCT Filed: Sep. 30, 2015

(86) PCT No.: PCT/US2015/053126
§ 371 (c)(1),
(2) Date: Mar. 30, 2017

(87) PCT Pub. No.: WO2016/054151
PCT Pub. Date: Apr. 7, 2016

(65) Prior Publication Data
US 2017/0295825 A1   Oct. 19, 2017

Related U.S. Application Data

(60) Provisional application No. 62/057,484, filed on Sep. 30, 2014.

(51) Int. Cl.
*G01N 33/02* (2006.01)
*G09B 19/00* (2006.01)

(52) U.S. Cl.
CPC ......... *G01N 33/02* (2013.01); *G09B 19/0092* (2013.01)

(58) Field of Classification Search
None
See application file for complete search history.

(56) References Cited

U.S. PATENT DOCUMENTS

| | | |
|---|---|---|
| 5,887,749 A | 3/1999 | Schommer et al. |
| 5,925,390 A | 7/1999 | Kornacki |

(Continued)

FOREIGN PATENT DOCUMENTS

| | | |
|---|---|---|
| DE | 29711410 U1 | 9/1997 |
| EP | 0769252 A1 | 4/1997 |

(Continued)

OTHER PUBLICATIONS

Koppel. Sensory Analysis of Pet Foods. J Sci Food Agric Feb. 4, 2014, pp. 1-6). (Year: 2014).*

(Continued)

*Primary Examiner* — Olivia M. Wise
(74) *Attorney, Agent, or Firm* — Baker Botts L.L.P.

(57) ABSTRACT

Refusal-based methods of establishing a cat or dog food preference, which can include methods of selecting a preferred cat or dog food among multiple foods as well as methods of determining palatability are provided. The methods can include presenting a cat or dog with one or more small samples of a test food and observing for refusal behavior, which can include refusing to eat a food sample. Higher numbers of instances of refusal of a particular food can be correlated with lower palatability.

12 Claims, 16 Drawing Sheets

(56) References Cited

U.S. PATENT DOCUMENTS

| | | | |
|---|---|---|---|
| 6,203,825 | B1 | 3/2001 | Hodgkins |
| 6,355,612 | B1 | 3/2002 | Ballevre et al. |
| 6,410,063 | B1 | 6/2002 | Jewell et al. |
| 6,669,975 | B1 | 12/2003 | Abene et al. |
| 7,585,533 | B2 | 9/2009 | Fritz-Jung et al. |
| 7,731,996 | B2 | 6/2010 | Bruce et al. |
| 8,029,819 | B2 | 10/2011 | Bierer et al. |
| 8,088,420 | B2 * | 1/2012 | Hall .................... A23K 50/40 426/2 |
| 8,529,940 | B2 | 9/2013 | Sunvold et al. |
| 2001/0048955 | A1 | 12/2001 | Foreman et al. |
| 2003/0026875 | A1 | 2/2003 | Aguilar et al. |
| 2003/0026876 | A1 | 2/2003 | Albuja et al. |
| 2003/0194423 | A1 | 10/2003 | Torney et al. |
| 2004/0005388 | A1 | 1/2004 | Bruce et al. |
| 2004/0047898 | A1 | 3/2004 | Harper et al. |
| 2004/0197462 | A1 * | 10/2004 | Hall .................... A23K 40/00 426/620 |
| 2004/0208979 | A1 * | 10/2004 | Miller .................. A23K 40/00 426/656 |
| 2004/0244068 | A1 | 12/2004 | Heaton et al. |
| 2008/0038403 | A1 | 2/2008 | Bierer et al. |
| 2008/0089984 | A1 | 4/2008 | Bruce et al. |
| 2017/0188548 | A1 * | 7/2017 | Rogues ................ G06Q 30/02 |

FOREIGN PATENT DOCUMENTS

| | | |
|---|---|---|
| GB | 2079579 A | 1/1982 |
| JP | H1014501 A | 1/1998 |
| JP | 2002238464 A | 8/2002 |

OTHER PUBLICATIONS

"Nutrient Requirements of Dogs and Cats, Chapter 3, Energy", National Research Council of the National Academies, 2006, 23 pps.

Boissy, et al., "Assessment of Positive Emotions in Animals to Improve Their Welfare", Physiology & Behavior, 92 (2007), 375-397.

Bradshaw, "Food Selection by the Domestic Cat, an Obligate Carnivore", Compl. Biochem. Physiol., 114A, 3:205-209, 1996.

Burman, et al., "Sensitivity to Reward Loss as an Indicator of Animal Emotion and Welfare", Biol. Lett. (2008), 4, 330-333.

Burman, et al., "The Influence of Preexperimental Experience on Social Discrimination in Rats (Rattus norvegicus)", Journal of Comparative Psychology, 2003, vol. 117, No. 3, pp. 344-349.

Dawkins, "From an Animal's Point of View: Motivation, Fitness and Animal Welfare", Behavioral and Brain Sciences (1990), 13, 1-61, pp. 1-9.

Mendl, "Performing Under Pressure: Stress and Cognitive Function", Applied Animal Behaviour Science, 65 (1999), 221-244.

Nicol, et al., "Associations between Welfare Indicators and Environmental Choice in Laying Hens", Animal Behavior, 78 (2009), pp. 413-424.

Spruijt, et al., "A Concept of Welfare Based on Reward Evaluating Mechanisms in the Brain: Anticipatory Behaviour as an Indicator for the State of Reward Systems", Applied Animal Behaviour Science, 72 (2001), 145-171.

Stasiak, The Effect of Early Specific Feeding on Food Conditioning in Cats, Developmental Psychobiology, Wiley and Sons, New York, NY, vol. 39, Jan. 1, 2001, pp. 207-215, XP002314252.

Tami, et al., "A Model to Quantify the Anticipatory Response in Cats", Animal Welfare, 2011, 20:191-200.

Thorne, Feeding Behaviour in the cat—recent advances., Journal of Small Animal Practice, vol. 23, No. 9, Apr. 10, 2008, p. 555-562, XP055235101.

Tobie, et al., Assessing Food Preferences in Dogs and Cats; A review of the Current Methods., Animals, Mar. 1, 2015, pp. 1-8, XP055235359, Retrieved from: http://www.ncbi.nlm.nih.gov/pmc/articles/PMC4494339/.

Van Den Bos, et al., "Anticipation is Differently Expressed in Rats (Rattus norvegicus) and Domestic Cats (Felis silvestris catus) in the same Pavlovian Conditioning Paradigm", Behavioural Brain Research, 141 (2003), 83-89.

Nilkie, et al., "Errors Made by Animals in Memory Paradigms are not always due to Failure of Memory", Neuroscience and Biobehavioral Reviews, 23 (1999) 451-455.

Promotional Material regarding the Macronutrient Profile of the Optimum Brand, Mars Petcare, The Waltham Centre for Pet Nutrition, Waltham on the Wolds, GB, Dec. 20, 2006, 16 pgs.

The Waltham Book of Dog and Cat Behavior, Ed., C. Thorne, Pergamon Press, PLC, Oxford England, p. 118, 1992.

Bradshaw, "Sensory and Experimental factors in the Design of Foods for Domestic Dogs and Cats", Proceedings of the Nutrition Society (Mar. 1991) 50, 99-106.

Burger, "Feeding", Catlopaedia, 49-91, Howell Book House, New York, NY, US, 1997.

Lester, et al., "Macronutrient Utilization in Cats Fed Low and High Fat Diets", FASEB Journal, vol. 11, No. 3, Nov. 1997, p. A372, Abstract 2156.

Rice, "The Dog Handbook", pp. 48-49, published by Barron's Educational Series, Oct. 1, 1999.

Romsos, et al., "Regulation of protein intake in adult dogs", JAVMA, vol. 182(1), pp. 41-43, Jan. 1983.

Serpell, "The Domestic Dog", published by Cambridge University Press, pp. 104-106, Sep. 1995.

Thorne, "Feeding Behavior of Cats", Cat World (May 1992), 171:20-21.

Wills, "Adult Maintenance", BSAVA Manual of Companion Animal Nutrition & Feeding, Chapter 3, British Small Animal Veterinary Association, Shurdington, Cheltenham, UK, Apr. 19, 1996, pp. 44-46.

Wills, et al., "Basic Principles of Nutrition and Feeding", BSAVA Manual of Companion Animal Nutrition and Feeding, Apr. 19, 1996, British Small Animal Veterinary Association, Shurdington, Cheltenham, UK, Chapter 1, pp. 10-21.

* cited by examiner

REFUSAL-BASED METHODS OF ESTABLISHING A CAT OR DOG FOOD PREFERENCE

CROSS-REFERENCE TO RELATED APPLICATIONS

This application claims priority to U.S. Provisional Patent Application Ser. No. 62/057,484, filed Sep. 30, 2014, the contents of which are incorporated by reference herein in their entirety.

FIELD

The presently disclosed subject matter relates to refusal-based methods of establishing a cat or dog food preference, which can include methods of selecting a preferred cat or dog food among multiple foods as well as methods of determining palatability.

BACKGROUND

Cat and dog foods can be defined broadly to include both wet and dry foods as well as cat and dog treats, cat and dog care products (including edible veterinary and dental products), and raw materials incorporated into pet foods and other foods. The palatability of cat and dog foods and cat and dog preferences among different cat and dog foods are important factors that can determine how much of a food a cat or dog will eat. Management of cat and dog nutrition and diet can be essential to good health and longevity of domestic cats and dogs. Better understanding and optimization of the palatability of cat and dog foods can help to improve cats and dogs nutrition and diet and prevent obesity. High palatability of a cat and dog food can encourage reliable, regular consumption of the food and can facilitate administration of the food to the animal. High palatability can be important in inducing cats and dogs to consume cat and dog care products that benefit their health, e.g., veterinary products and dental chews.

Existing methods for determining the palatability of cat and dog foods and cats and dogs preferences among different foods are often intake-based. Examples of intake-based methods include monadic intake tests, choice/preference tests, and monadic intake tests with repeated exposures over time. All such methods correlate the quantity consumed of a particular food with its palatability. Quantity of consumption can be measured through weighing of a food sample before and after eating, or by other methods. Intake-based methods of determining cat and dog food palatability and preference can have certain drawbacks. For example, the quantity of food eaten may not perfectly reflect animal satisfaction, contentment, and preference. The ideal cat or dog food can be one that leaves a cat or dog feeling satiated and satisfied without inducing overeating; foods eaten in the largest quantities may encourage undesirable animal obesity. Intake-based methods can have high variability, which can require large sample sizes (i.e., large numbers of subject animals). Comparison of the palatability of foods of different densities and weights (e.g., wet foods and dry foods) can be challenging or unreliable with intake-based methods. Finally, intake-based methods can require use of large numbers of cats or dogs when untrained house pets are used.

Thus, there remains a need in the art for improved methods of determining cat and dog food palatability and establishing cat and dog food preferences.

SUMMARY OF THE DISCLOSED SUBJECT MATTER

An exemplary method of establishing a cat and dog food preference can include measuring refusal in a cat or dog subject.

An exemplary method of selecting a preferred cat or dog food can include establishing a baseline of food receptiveness. Establishing a baseline of food receptiveness can include the steps of presenting a sample of a high value contrast food to a cat or dog, removing the sample of the high value contrast food after a set duration of time, t1, and recording instances of refusal of the high value contrast food. Each step can optionally be repeated one or more times. Establishing a baseline of food receptiveness can further include computing a total number of instances of refusal of the high value contrast food. The method can further include introducing a first test food. Introducing a first test food can include the steps of presenting a sample of a first test food to the cat or dog, removing the sample of the first test food after the set duration of time, t1, and recording instances of refusal of the first test food. Each step can optionally be repeated one or more times. Introducing a first test food can further include computing a total number of instances of refusal of the first test food. The method can further include again establishing a baseline of food receptiveness. Reestablishing a baseline of food receptiveness can include the steps of presenting a sample of a high value contrast food to a cat or dog, removing the sample of the high value contrast food after the set duration of time, t1, and recording instances of refusal of the high value contrast food. Each step can optionally be repeated one or more times. Reestablishing a baseline of food receptiveness can further include computing a total number of instances of refusal of the high value contrast food. The method can further include introducing a second test food. Introducing a second test food can include the steps of presenting a sample of a second test food to the cat or dog, removing the sample of the second test food after the set duration of time, t1, and recording instances of refusal of the second test food. Each step can optionally be repeated one or more times. Introducing a second test food can further include computing a total number of instances of refusal of the second test food. The method can further include selecting a preferred cat or dog food between the first test food and the second test food based on a lower total number of instances of refusal.

An exemplary method of selecting a preferred cat or dog food can include establishing a baseline of food receptiveness to a first test food. Establishing a baseline of food receptiveness to a first test food can include the steps of presenting a sample of a first test food to a cat or dog, removing the sample of the first test food after a set duration of time, and recording instances of refusal of the first test food. Each step can optionally be repeated one or more times. The method can further include introducing a first disruption in food receptiveness. Introducing a first disruption in food receptiveness can include the steps of presenting a sample of a high value contrast food to the cat or dog, removing the sample of the high value contrast food after the set duration of time, t1, and recording instances of refusal of the high value contrast food. Each step can optionally be repeated one or more times. Introducing a first disruption in food receptiveness can further include computing a total number of instances of refusal of the high value contrast food. The method can further include reintroducing the first test food to the cat or dog. Reintroducing the first test food to the cat or dog can include the steps of presenting a sample of the first test food to the cat or dog, removing the sample of the first test food after the set duration of time, t1, and recording instances of refusal of the first test food. Each step can optionally be repeated one or more times. Reintroducing the first test food to the cat or dog can further include computing a total number of instances of refusal of the first test food. The method can further include establishing a baseline of food receptiveness to a second test cat or dog food. Establishing a baseline of food receptiveness to a second test cat or dog food can include the steps of presenting a sample of a second test food to a cat or dog, removing the sample of the second test food after the set duration of time, t1, and recording instances of refusal of the second test food. Each step can optionally be repeated one or more times. The method can further include introducing a second disruption in food receptiveness. Introducing a second disruption in food receptiveness can include the steps of presenting a sample of the high value contrast food to the cat or dog, removing the sample of the high value contrast food after the set duration of time, t1, and recording instances of refusal of the high value contrast food. Each step can optionally be repeated one or more times. Introducing a second disruption in food receptiveness can further include computing a total number of instances of refusal of the high value contrast food. The method can further include reintroducing the second test food to the cat or dog. Reintroducing the second test food to the cat or dog can include the steps of presenting a sample of the second test food to the cat or dog, removing the sample of the second test food after the set duration of time, t1, and recording instances of refusal of the second test food. Each step can optionally be repeated one or more times. Reintroducing the second test food to the cat or dog can further include computing a total number of instances of refusal of the second test food. The method can further include selecting a preferred test food between the first test food and the second test food based on a lower total number of instances of refusal.

In certain embodiments, the cat or dog can be an untrained house cat or dog. In certain embodiments, the methods of the present disclosure can include presenting the cat or dog with one or more anticipatory cues that signal feeding prior to submitting samples of the first cat or dog food and the second food. In certain embodiments, refusal can be selected from the group consisting of refusal to approach a food sample, refusal to begin eating a food sample, refusal to finish eating a food sample, and combinations thereof. In certain embodiments, all steps of the methods of the present disclosure can be performed within one day. In certain embodiments, the method can be automated.

In certain embodiments, the first cat or dog food and the second cat or dog food can be independently selected from the group consisting of dry cat or dog foods, wet cat or dog foods, cat or dog treats, cat or dog care products, raw materials for dry cat or dog foods, raw materials for wet cat or dog foods, and combinations thereof. In certain embodiments, the first test food and the second test food can be different.

DETAILED DESCRIPTION

Figure 1:
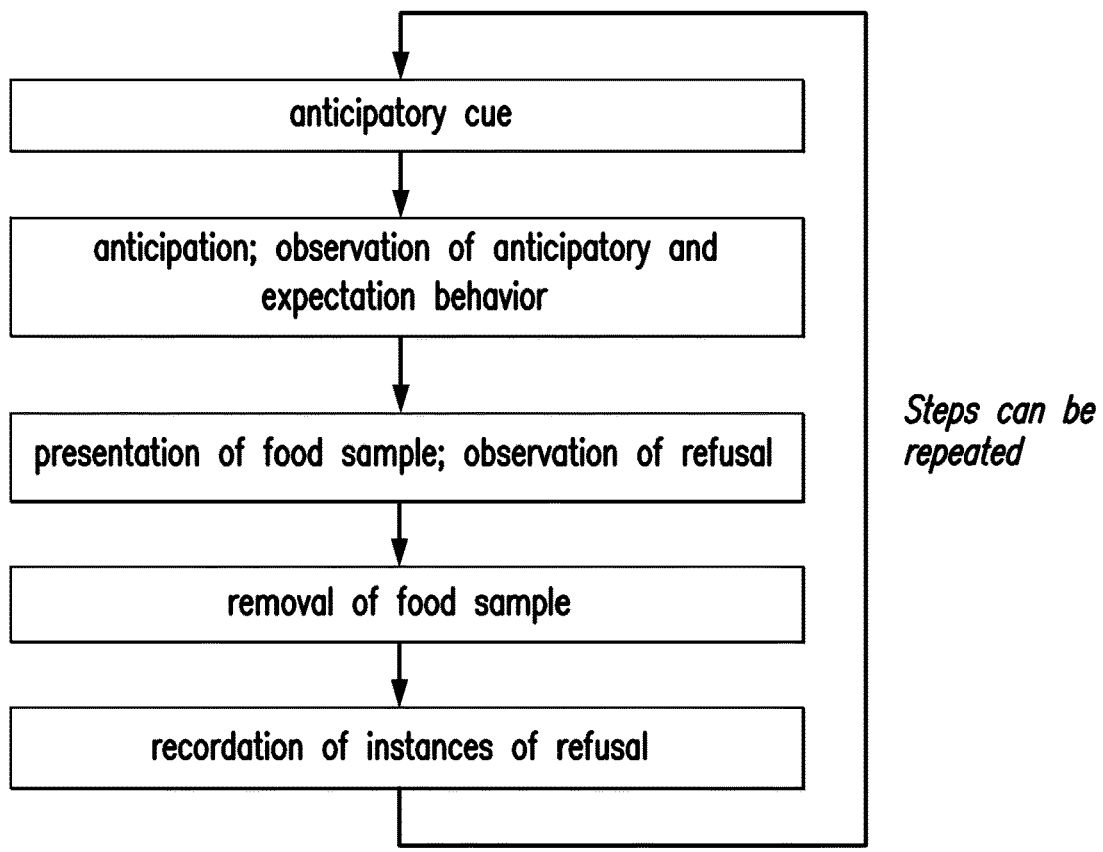
FIG. 1 is a schematic diagram showing an exemplary protocol for one or more trials conducted in conjunction with the presently disclosed methods.

To date, there remains a need in the art for improved methods of determining cat or dog food palatability and establishing cat or dog food preferences. The present disclosure provides refusal-based methods of establishing a cat or dog food preference, which can include methods of selecting a preferred cat or dog food among multiple foods as well as methods of determining palatability. These methods are not intake-based and do not require weighing of food before and after consumption. The presently disclosed methods can have important advantages over existing methods of determining cat or dog food palatability and establishing cat food preferences.

For clarity and not by way of limitation, the detailed description is divided into the following subsections: I. Definitions; II. Feline and Canine Subjects; III. Test Foods; IV. Refusal Behavior; V. Protocol; and VI. Analysis.

I. Definitions

As used herein, the words "a" or "an," when used in conjunction with the term "comprising" in the claims and/or the specification, may mean "one," but they are also consistent with the meaning of "one or more," "at least one," and/or "one or more than one." Furthermore, the terms "having," "including," "containing" and "comprising" are interchangeable, and one of skill in the art will recognize that these terms are open ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As used herein, the term "palatability" refers to a food's appeal and acceptability to a subject's taste and palate. Palatable foods are foods that are appealing and acceptable to a subject. Palatability can be relative, such that some foods are highly palatable, i.e., highly appealing and desirable, whereas other foods are less palatable, i.e., less appealing and desirable. The subject can prefer more palatable foods over less palatable foods.

As used herein, the term "preferred" means favored. A preferred cat or dog food can be a cat or dog food that cats and dogs tend to choose over other foods. As described above, a preferred cat or dog food can be a cat or dog food of relatively high palatability compared to other cat or dog foods.

As used herein, the term "satiated" means satisfied or full as to a subject's appetite or desire.

As used herein, the terms "metabolic energy requirement" or "maintenance energy requirement" ("MER") mean the amount of energy used by a subject in a thermoneutral or ambient temperature environment. MER represents the energy expended in obtaining and using food in amounts sufficient to maintain body weight, but not support growth, pregnancy or lactation. MER includes energy needed to obtain, digest, and absorb foods as well as energy for spontaneous activity. Calculations for MER take into account age and neuter status. MER calculations are further explained in "Nutrient requirements of dogs and cats," Animal Nutrition Series (National Research Council of the National Academies; Chapter 3, Energy), the disclosure of which is incorporated herein in its entirety.

As used herein the term "standard meal" refers to a meal that contains the daily Nutritional requirements for a subject, such as a cat or a dog. Daily Nutritional requirements are further explained in "Nutrient requirements of dogs and cats," Animal Nutrition Series (National Research Council of the National Academies; Chapter 3, Energy), the disclosure of which is incorporated herein in its entirety.

II. Feline & Canine Subjects

The presently disclosed methods can involve observation and study of feline or canine subjects. Cats and dogs that can be used as subjects in connection with the methods of the present disclosure can include domestic cats (*felis catus*) or dogs (*Canis*). The cats and dogs can include both untrained and trained cats and dogs. Untrained cats or dogs can include ordinary household pets. Trained cats and dogs can include cats kept in a cattery or dogs kept in kennels. Trained cats or dogs can include cats and dogs trained for use in nutrition studies, e.g., cats or dogs fed a standardized diet.

Cats and dogs that can be used as subjects in connection with the methods of the present disclosure can include both male and female cats and dogs. In certain embodiments, cats used as subjects can be kittens and the dogs used as subjects can be puppies, e.g., cats or dogs younger than about one (1) year old. In certain embodiments, cats and dogs used as subjects can be non-elderly, healthy adult cats, e.g., cats or dogs between about one (1) year and about 6, about 7, about 8, about 9, about 10, about 11, about 12, about 13, about 14, or about 15 years old. In certain embodiments, cats or dogs used as subjects can be between about one (1) year and about 8 years old. In certain embodiments, cats or dogs used as subjects can be between about two (2) years and about 13 years old. In certain embodiments, cats or dogs used as subjects can be selected for oral health (i.e., free from dental problems).

In certain embodiments, cats or dogs used as subjects can be unhealthy cats suffering from a disease and/or disorder and in need of a specialized or convalescence diet. In certain embodiments, cats or dogs used as subjects can be senior or elderly cats or dogs, e.g., cats older than about 10, about 11, about 12, about 13, about 14, or about 15 years old or dogs older than about 6, about 7 about 8 about 9, about 10, about 11, about 12, about 13, about 14, or about 15 years old.

In certain embodiments of the presently disclosed subject matter, the cats or dogs used as subjects can be satiated prior to the start of the test. By way of non-limiting example, cats or dogs used as subjects can be fed about 50% of their metabolic (or maintenance) energy requirement (MER) prior to testing. By way of non-limiting example, cats or dogs used as subjects can be fed a standard meal prior to testing or, for cats or dogs fed twice daily, can be fed a standard ½ daily ration.

In certain embodiments, use of satiated cats or dogs can improve the quality of the presently disclosed methods. For example, satiated cats or dogs can be more "picky" and selective among different foods. Consequently, the sensitivity of methods of determining palatability, establishing a cat or dogs food preference, and selecting a preferred cat or dog food among two or more foods can be increased. By contrast, hungry, or not-satiated, cats or dogs may readily eat samples of foods that are of only moderate or even of low palatability.

III. Test Foods

Certain cat and dog foods can be used as test foods in the methods of the present disclosure. As noted in the Background, cat or dog foods can be defined broadly to include both wet and dry foods as well as cat or dog treats, cat or dog care products (including edible veterinary and dental products), and raw materials incorporated into wet and dry foods. Exemplary wet foods can include canned cat or dog foods, wet foods packaged in foil pouches, wet foods packaged in plastic trays, raw cat or dog foods, and thawed frozen cat or dog foods. Exemplary dry foods can include bagged and other packaged cat or dog foods (e.g., kibble, pellets, flakes). Exemplary cat or dog treats can include semi-moist treats (e.g., cat sticks or dog strips) and pockets (e.g., crispy pockets with soft centers). Exemplary cat or dog care products can include oral veterinary products (e.g., edible medicines) and dental chews (e.g., teeth-cleaning products).

Cat and dog foods can generally be prepared from various raw materials known in the art. Certain raw materials can also be tested themselves in accordance with the methods of the present disclosure, and certain raw materials can be fed directly to cats or dogs. By way of non-limiting example, raw materials can include fish (e.g., tuna, whitefish, salmon, sardine, herring, anchovy), poultry (e.g., chicken, turkey), meat (e.g., cow, pig, goat, sheep, horse), offal of various species (e.g., liver, kidney, heart, lung, intestines), dairy products, grains, vegetables, and combinations thereof. Raw materials can also include other protein, carbohydrate, and/or fat sources (e.g., raw materials of microbial origin).

Certain cat and dog foods can be used as high value contrast foods. Such foods can include foods known to be highly palatable and highly desirable to cats or dogs. High value contrast foods can be characterized by cats' or dogs' willingness to continue eating samples of the foods. High value contrast foods can also be denoted simply as "high value" foods or "contrast" foods. By way of non-limiting example, high value contrast foods can include processed or canned tuna of various species (e.g., canned tuna in spring water or oil). By way of non-limiting example, high value contrast foods can include commercial cat and dog foods that are known to be highly palatable and highly desirable to cats or dogs.

In certain embodiments of the presently disclosed subject matter, samples of cat or dog food can be presented to a cat or dog. Suitable samples can be small samples of the cat or dog food, e.g., individual pieces of kibble. Small samples of food can be cut from larger pieces. Standardized samples of a food can be prepared. By of non-limiting example, standardized portions of a wet food or other cat or dog food can be weighed out during preparation to ensure that each sample is of approximately similar size. A sample of a cat or dog food can include one or more pieces of the food. For example, a sample of a cat or dog food can include one, two, three, four, five, or more than five pieces of the food. In certain embodiments, a sample of a cat or dog food can include two pieces or three pieces of the food, e.g., two or three pieces of kibble.

Samples of cat or dog food can be presented in various ways. For example, samples can be presented in a standardized bowl, in a non-standardized bowl (e.g., a house cat's or dog's feeding bowl), in a standardized dish, in a non-standardized dish (e.g., a house cat's or dog's dish), on a floor surface, or in a human's hand.

IV. Refusal Behavior

Observation and recording of cats' or dogs refusal of a food can be an important part of the methods of the present disclosure. Refusal of a particular food can indicate disinterest, distaste, and/or dislike for the food. A cat's or dog's decision to eat a first food and to refuse a second food can indicate that the first food has a higher palatability than the second food and is preferred to the second food.

The term "refusal" is herein used to encompass various behaviors related to refusal of a food. A cat's or dog's refusal of a food can take different forms. In certain embodiments, refusal can be selected from the group consisting of refusal to approach a food sample, refusal to begin eating a food sample, refusal to finish eating a food sample, and combinations thereof. Refusal can be measured as instances of refusal. In certain embodiments, instances of refusal can be measured as instances in which a cat or dog declines to eat a food sample within a set presentation period, e.g., 30 seconds. For example, one presentation period in which a cat or dog declines to eat a given food sample can constitute one instance of refusal. Failure to finish a food sample can constitute an instance of refusal; i.e., a cat's or dog's partial consumption of a food sample within a set presentation period can constitute an instance of refusal. By way of non-limiting example, in certain embodiments wherein a food sample contains more than one piece of food, consumption of some but not all of the pieces of food can constitute an instance of refusal.

V. Protocol

Test area. The presently disclosed methods can be carried out in various locations. By way of non-limiting example, the presently disclosed methods can be carried out in a home, in a cattery, in a kennel, or in a veterinary setting. The presently disclosed methods can be carried out indoors or outdoors.

Observation of cats and dogs. Cats and dogs can be observed and their behavior can be monitored by various techniques known in the art. In certain embodiments, cats or dogs can be observed by one or more cameras recording their behavior. In certain embodiments, cats or dogs can be observed by human observers.

Trials. Reference will now be made in detail to various exemplary embodiments of the disclosed subject matter, exemplary embodiments of which are illustrated in the accompanying drawings. By way of illustration and not limitation, FIG. 1 presents a schematic diagram of an exemplary protocol for one or more trials conducted in conjunction with the presently disclosed methods. The exemplary protocol can optionally include the steps of presenting a cat or dog with one or more anticipatory cues that signal feeding. The protocol can optionally include an "anticipation period" or "waiting period" after presentation of the anticipatory cue(s), during which the cat's or dog's anticipatory and expectation behavior can be observed. The protocol can include presentation of a food sample during a "presentation period." Food can be presented for a set duration of time, during which refusal behavior can be observed. The protocol can include removal of the food sample. The food sample can be removed after the set duration of time. The protocol can include recording of any refusal behavior (instances of refusal) that occurred during the presentation period. The protocol can optionally include repeating the foregoing steps one or more time. The protocol can optionally include an "inter-trial period" after the food sample is removed and before any subsequent steps are performed.

Anticipatory cues. In certain embodiments, the methods of the present disclosure can include presenting the cat or dog with one or more anticipatory cues that signal feeding prior to submitting food samples to the cat or dog, as shown in FIG. 1. Exemplary anticipatory cues can include visual cues, aural cues, and olfactory cues. By way of non-limiting example, visual cues can include showing a food sample to a cat or dog, visibly placing or moving a food bowl, and combinations thereof. Aural cues can include food-related sounds. Food-related sounds are sounds related to the preparation of food, the opening of food, and/or the serving of food. By way of non-limiting example, aural cues can include the sound of a can opening, the sound of kibbles being shaken in a bag or other container, and/or the sound of a food sample being placed in a bowl. Aural cues can also include training cues, e.g., the sound of a clicker. By way of non-limiting example, olfactory cues can include one or more smells related to the preparation of food, the opening of food, and/or the serving of food. The cat or dog can be provided with one or more anticipatory cues over a short period of time, e.g., about one second, about two seconds, about three seconds, about four seconds, about five seconds, or about ten seconds.

In certain embodiments, the anticipatory cues can be cues that a particular cat or dog subject is accustomed to. For example, if the cat or dog subject is an untrained house cat or dog, the anticipatory cues can be existing visual, aural, and/or olfactory cues that the house cat or dog associates with feeding.

Anticipation. If the cat or dog is presented with one or more anticipatory cues that signal feeding prior to submitting food samples to the cat or dog, the cat's and dog's anticipatory and expectation behavior can then be observed, as shown in FIG. 1. The period after which the cat or dog is presented with anticipatory cue(s) but before the cat or dog is presented with a food sample can be termed an "anticipation period" or "waiting period." The anticipation period can be a set duration of time. In certain embodiments the anticipation period can be between about 5 seconds and about 60 seconds, e.g., about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds. In certain embodiments, the anticipation period can be about 30 seconds.

In certain embodiments, the anticipation period can be less than about 5 seconds or zero seconds. In other words, in certain embodiments the anticipation period can be optional, and presentation of a food sample can immediately follow any anticipatory cues.

In certain embodiments of the methods of the presently disclosed subject matter wherein more than one kind of food sample is presented, the anticipation period can be the same or different for each kind of food sample. For example, in methods involving a first test food, a second test food, and a high value contrast food, the anticipation period can be the same for the first test food and the second test food but can be different for the high value contrast food. In certain embodiments, the anticipation period Presentation of a food sample. A food sample can be presented (distributed) to a cat or dog subject during a "presentation period." The food sample can be presented as described above, e.g., in a standardized dish or bowl. In certain embodiments, food sample can be placed and left in a consistent location, e.g., at a permanent location on the floor of a test area.

The food sample can be presented for a set duration of time, during which refusal behavior can be observed. When the presentation period is of a set duration of time, the duration of time can be denoted t1. In certain embodiments the presentation period t1 can be between about 5 seconds and about 60 seconds, e.g., about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds. In certain embodiments, and as described in the Examples, the presentation period t1 can be 30 seconds. During the presentation period, the cat or dog can have an opportunity to investigate, taste, and eat the food sample, even if the cat or dog was uninterested at first presentation.

Removal of the food sample. After the presentation period, the food sample can be removed. Any uneaten pieces of food can be removed. Any uneaten pieces of food can be evidence of refusal. The feeding area can be cleaned to remove any residue associated with the food sample.

Recording of instances of refusal. Instances of refusal of the food sample during the presentation period can be recorded. That is, any refusal behavior (as described above) can be tallied to provide a count of instances of refusal associated with the food sample in the trial.

Method designs. In certain embodiments of the presently disclosed methods, multiple trials can be conducted. In certain embodiments, multiple trials can be conducted with multiple cats or dogs. In certain embodiments, multiple trials can be conducted with the same cat or dog. As shown in FIG. 1, the steps of presenting a cat or dog with one or more anticipatory cues that signal feeding, observing anticipatory and expectation behavior of the cat or dog, presenting a sample of food to the cat or dog and observing refusal behavior, removing the sample of food, and recording instances of refusal can optionally be repeated one or more times. In certain embodiments, the steps of presenting a sample of food to the cat or dog and observing refusal behavior, removing the sample of food, and recording instances of refusal can optionally be repeated one or more times.

It can be advantageous to conduct multiple trials to improve the accuracy and reproducibility of the methods of the present disclosure. In certain embodiments, trials can be conducted with multiple animals at once. For example, trials can be conducted with groups of cats or dogs. The groups of cats or dogs can include from about three to about 100 cats or dogs. In certain embodiments, trials can be conducted with a group of cats or dogs that includes about 10 to about 50 animals, e.g., about 10, about 12, about 15, about 20, about 25, about 30, about 35, about 40, about 45, or about 50 animals.

In certain embodiments, multiple trials can be conducted with one cat or dog. The trial protocol can optionally include an "inter-trial period" after the food sample is removed and before any subsequent steps are performed. For example, in certain embodiments of the presently disclosed methods, an inter-trial period can be provided between removal of the food sample from a first trial and commencement of a second trial, i.e. presentation of an anticipatory cue or an additional food sample. In certain embodiments, there can be no inter-trial period, and a second trial can commence immediately after removal of the food sample from the first trial. The optional inter-trial period can vary from about 1 second to about 60 seconds. For example, in certain non-limiting embodiments, the inter-trial period can be about 1 second, about 3 seconds, about 5 seconds, about 10 seconds, about 15 seconds, about 20 seconds, about 30 seconds, about 40 seconds, about 50 seconds, or about 60 seconds.

In certain embodiments wherein multiple trials are conducted with one cat or dog, the cat or dog can participate in many trials in a single day. By way of non-limiting example, a cat or dog can participate in about 5, about 10, about 15, about 20, about 25, about 30, about 35, about 40, about 45, or about 50 trials in a single day.

In certain embodiments of the presently disclosed methods where multiple trials are conducted with one cat or dog, the methods can include providing a relatively long interval of no food presentation for a set duration of time, t2, during which the cat or dog is not presented with food. During this time the cat's or dog's appetite and expectations can be "reset." This period of time can be characterized as a "reset period." In certain embodiments, the reset period can be between about 5 minutes and about 5 days, e.g., about 5 minutes, about 10 minutes, about 20 minutes, about 30 minutes, about 45 minutes, about 60 minutes, about 90 minutes, about 2 hours, about 3 hours, about 4 hours, about 6 hours, about 8 hours, about 12 hours, about 18 hours, about 24 hours, about 36 hours, about 2 days, about 3 days, about 4 days, about 5 days, about 6 days, or about 7 days. After the set duration of time t2, the cat or dog can be fed to satiation, and further trials can be conducted.

In certain embodiments where multiple trials are conducted with one cat or dog, the methods can include particular trial designs. For example, in a "contrast alone" trial design, a cat or dog can be subjected to one or more trials with a high value contrast food, to establish a baseline of food receptiveness, and then subjected to one or more trials with a first test food, to determine relative palatability of the first test food. Additionally, a cat or dog can be subjected to one or more trials with the high value contrast food, to establish a baseline of food receptiveness, and then subjected to one or more trials with a second test food, to determine relative palatability of the second test food. In certain embodiments of the "contrast alone" trial design, the cats or dogs can, for each test food, be subjected to five (5) trials with the high value contrast food followed by ten (10) trials with the test food.

In a "mixed design" trial design, a cat or dog can be subjected to one or more trials with a first test food, to establish a baseline of food receptiveness to the first food; then subjected to one or more trials with a high value contrast food, to introduce a first disruption in food receptiveness; and then subjected to one or more trials with the first test food, to reintroduce the first test food and establish receptiveness to the first test food. Additionally, a cat or dog can be subjected to one or more trials with a second test food, to establish a baseline of food receptiveness to the second food; then subjected to one or more trials with the high value contrast food, to introduce a second disruption in food receptiveness; and then subjected to one or more trials with the second test food, to reintroduce the second test food and establish receptiveness to the second test food. In certain embodiments of the "mixed design" trial design, the cats or dogs can, for each test food, be subjected to five (5) trials with the test food, followed by five (5) with the high value contrast food, followed by ten (10) trials with the test food.

In either of the foregoing exemplary trial designs, the cats and dogs subjected to trials with the first test food and the second test food can be the same or different. Total numbers of instances of refusal of the first test food and the second test food can be computed, as described below, and the cat or dog food with a lower total number of instances of refusal can be selected as the preferred cat food. The food with the lower total number of instances of refusal can be the more palatable cat or dog food.

The methods of the present disclosure are not limited to comparisons of two food samples. In certain embodiments, three, four, five, or more different food samples can be prepared. The palatability of three, four, five, or more different food samples can be determined. A preferred food sample can be selected among a group of three, four, five, or more different food samples on the basis of a low total number of instances of refusal, according to the methods of the present disclosure.

Presenting a cat or dog with a high value contrast food prior to presentation of a test food can improve the sensitivity of the cat's or dog's palate and preference. Without being bound to any particular theory, it is possible that presentation of a contrast food, including repeated trials with the contrast food, can build an expectation in the cat or dog that it will continue to receive the high value contrast food. In certain embodiments, building an expectation in the cat or dog can be described as establishing a baseline of food receptiveness—in this instance, a baseline of food receptiveness wherein the cat or dog expects to continue to receive the high value contrast food and may respond with disappointment or disinterest if presented with a less palatable, less appealing food. In certain embodiments, a cat or dog test subject may first be presented with one or more samples of a test food to establish a baseline of food receptiveness to the test food. The cat or dog can then be presented with one or more samples of a high value contrast food, to introduce a disruption in food receptiveness. The disruption can build an expectation in the cat or dog that it will continue to receive the high value contrast food.

When the cat or dog expects to continue to receive the high value contrast food, the cat or dog may decline to eat the test food on subsequent presentation if it finds the test food disappointing in comparison to the high value contrast food. Alternatively, the cat or dog may eat a test food on a first presentation, but the cat or dog may refuse to consume further samples of the test food. The cat or dog may react with disinterest or distaste when its expectation of another sample of the high value contrast food is disappointed and a less palatable test food is presented instead. However, when the test food is itself highly palatable, the cat or dog may consume the test food on a first presentation and continue to consume the test food.

Automation. In certain embodiments, the methods of the present disclosure can be automated. For example, as noted above, cats or dogs can be observed and monitor by camera, which can obviate the need for a human observer. In certain embodiments, samples can be dispensed automatically, e.g., by a dispenser machine.

VI. Analysis

The methods of the present disclosure can include measurement of refusal behavior. Measurement of refusal behavior can include computing a total of number of instances of refusal of a test food, based on recorded instances of refusal.

Computation of a total number of instances of refusal of a test food can include simple counting of all refusals of the test food, across all trials. By way of non-limiting example, computation of a total number of instances of refusal of a food can include counting a total number of uneaten samples of the food. In certain embodiments wherein trials are conducting according to a "mixed design," as described above, the total number of instances of refusal of a test food can be computed by counting refusals in trials occurring after reintroduction of the test food, i.e., after the disruption in food receptiveness by introduction of the high value contrast food, while ignoring any refusals in trials occurring before introduction of the high value contrast food.

When multiple cats or dogs are used, computation of a total number of instances of refusal of a test food can include calculation of a proportion or percentage of cats or dogs eating the food for each trial, e.g., 100%, 90%, 75%, or 50%. When multiple cats or dogs are used, computation of a total number of instances of refusal can be based on a "survival" model rather than simple counting of uneaten food samples. For example, in certain embodiments, when a test food is presented to multiple cats or dogs, computation of a total number of instances of refusal can include calculation of the number of cats or dogs who refuse the test food at least once.

Computation of a total number of instances of refusal of a test food can also include calculation of "first refusal," i.e., measurement of the number of samples a given cat or dog eats of a given test food before it refuses a sample of the food. In certain embodiments, first refusal can also be calculated based on an average number of occasions on which samples of a test food is eaten before it is refused for the first time. Further details of calculation of first refusal and determination of cat or dog food palatability and cat or dog food preference based on first refusal are provided in the Examples.

Computation of a total number of instances of refusal of a test food and correlation of refusal behavior with cat or dog food palatability and cat or dog food preference can subjected to statistical analysis. In certain embodiments, a significant difference in preference between two or more cat or dog foods can be established at a p-value of less than or equal to 0.05.

The methods of establishing a cat or dog food preference, selecting a preferred cat or dog food, and determining cat or dog food palatability of the present disclosure can have advantages over existing methods, e.g., intake-based methods. For example, as described above and in the Examples below, the presently disclosed methods do not require use of trained cats or dogs; untrained house cats or dogs can be used. The presently disclosed methods can be carried out in various locations, e.g., in a cattery, kennel or in a home. The presently disclosed methods can allow direct comparison of different food types, e.g., wet and dry food. The presently disclosed methods can be quicker than certain existing methods and can be completed within a single day. Subject cats or dogs can participate in many trials in one day. The presently disclosed methods can be automated. When groups of multiple cats or dogs are used, the presently disclosed methods can be conducted with smaller groups of cats or dogs than intake-based methods, e.g., with groups of about 5 to about 25 cats or dogs rather than groups of 25 or more. The presently disclosed methods can enable use of smaller amounts of food than existing intake-based methods. Because smaller amounts of food are tested, cat or dog foods of high caloric content and/or nutritionally incomplete foods (e.g., raw materials) can be tested without adversely affecting the health of the cat or dog subjects.

EXAMPLES

The presently disclosed subject matter will be better understood by reference to the following Examples, which are provided as exemplary of the invention and not by way of limitation.

Example 1

Refusal-Based Testing with Untrained House Cats

Fourteen (14) healthy adult cats were recruited for a refusal-based study to establish cat food preference. The group of cats included 10 male and 4 female cats. The cats varied in age from 2 to 13 years, with a mean age of 7.8 years. All cats had a history of being fed on dry food (meal fed). To prepare for the study, cats were pre-fed for at least 1 week with a standardized dry food, a chicken-flavored kibble. Some of the subject cats also received some wet food in parallel, but feeding of wet food was discontinued before testing began. The subject cats were divided into 6 subgroups.

Three sample foods were tested. Food A was a dry cat food formulated to have relatively high palatability, a highly flavored kibble. Food B was dry cat food formulated to have relatively moderate palatability, a plain kibble coated with a palatant and fat. Food C was a dry cat food formulated to have relatively low palatability, a plain kibble without any coating. Processed canned tuna was used as a high value contrast food.

Three sets of tests were designed (Test 1, 2, and 3). Each subgroup was studied 2 days in a row for 3 weeks. Cats had 5 days off in between pairs of study days. The subgroups were rotated through the 3 tests presented in Table 1.

TABLE 1

|  | Day 1: Anticipation (no high value contrast food) | Day 2: Contrast (with high value contrast food) |
| --- | --- | --- |
| Test 1 | Food A—15 trials | Contrast food—5 trials; then Food A—10 trials |
| Test 2 | Food B—15 trials | Contrast food—5 trials; then Food B—10 trials |
| Test 3 | Food C—15 trials | Contrast food—5 trials; then Food C—10 trials |

Figure 2:
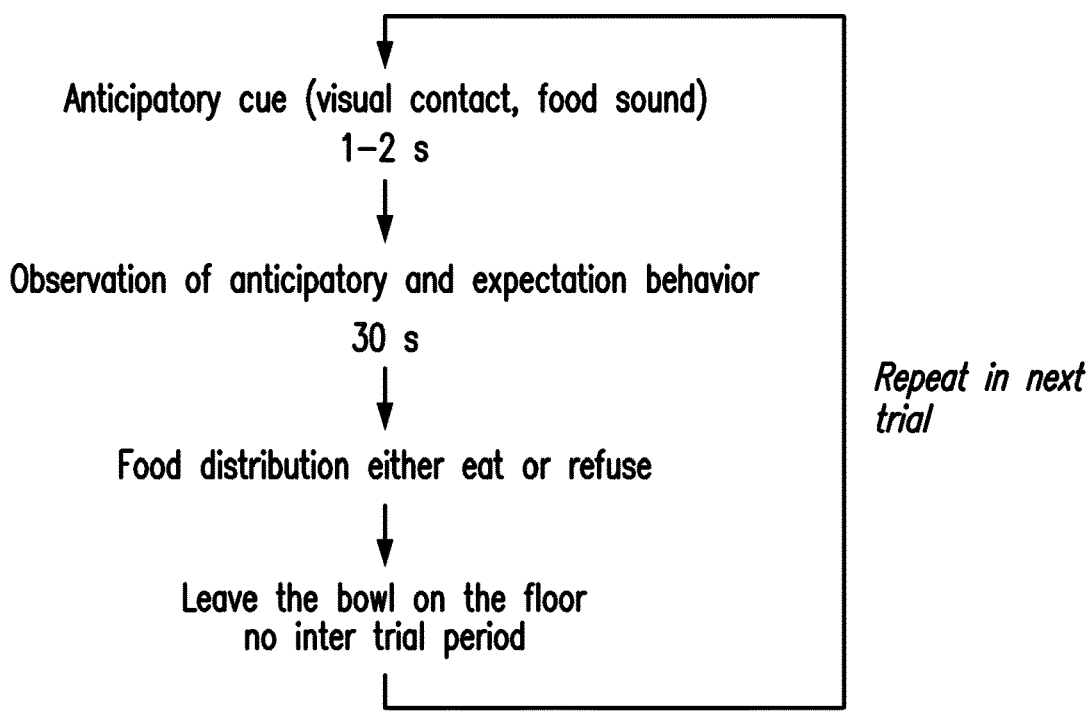
FIG. 2 is a schematic diagram showing another exemplary protocol for one or more trials conducted in conjunction with the presently disclosed methods.
Figure 3:
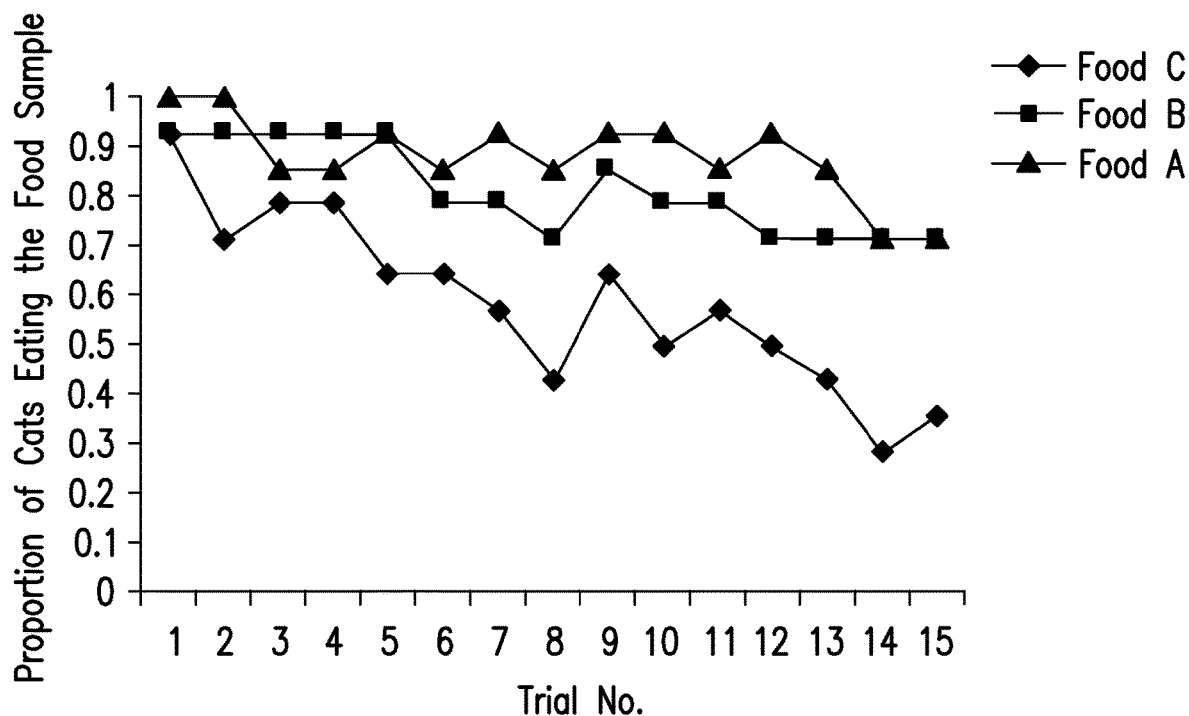
FIG. 3 presents results of an anticipation study according to an embodiment described in Example 1.
Figure 4:
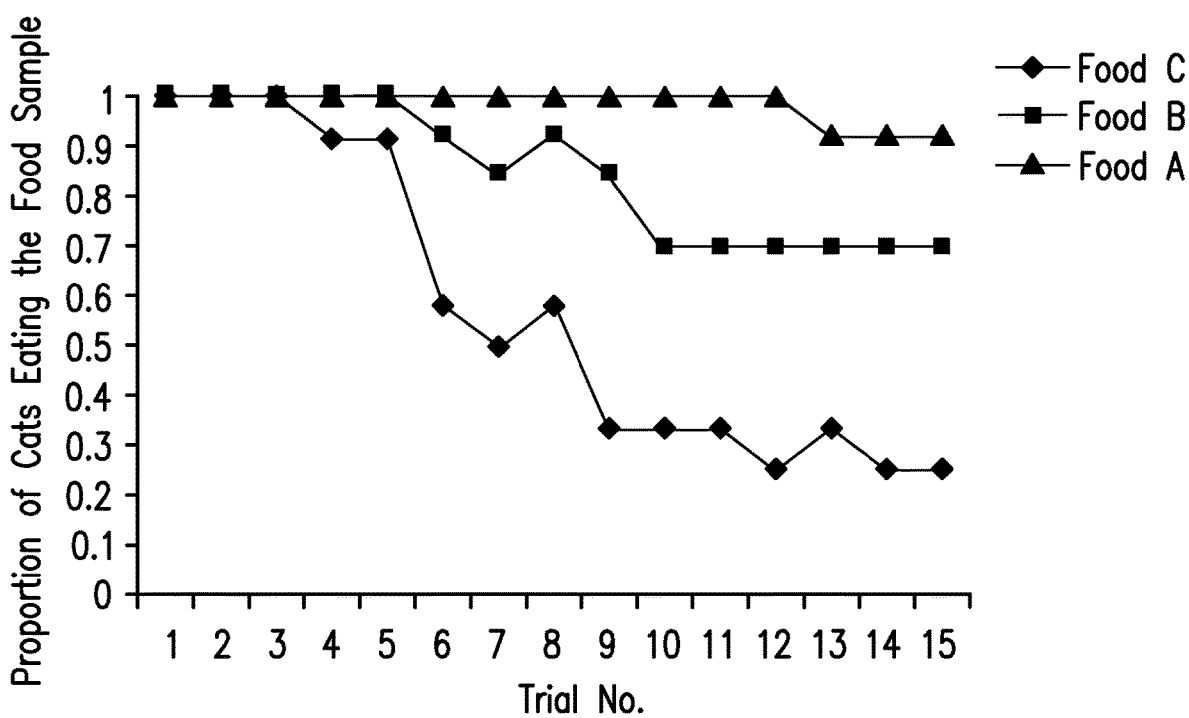
FIG. 4 presents results of a contrast study according to an embodiment described in Example 1.
Figure 5:
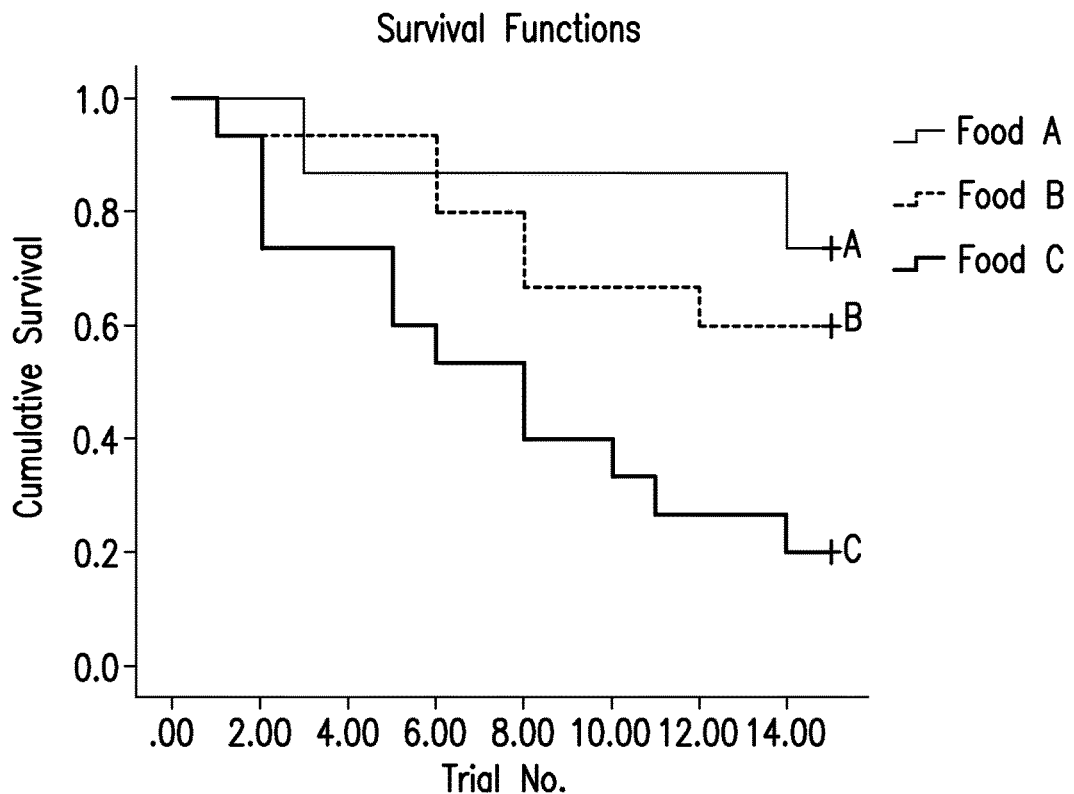
FIG. 5 depicts survival curves for the anticipation studies in Example 1.
Figure 6:
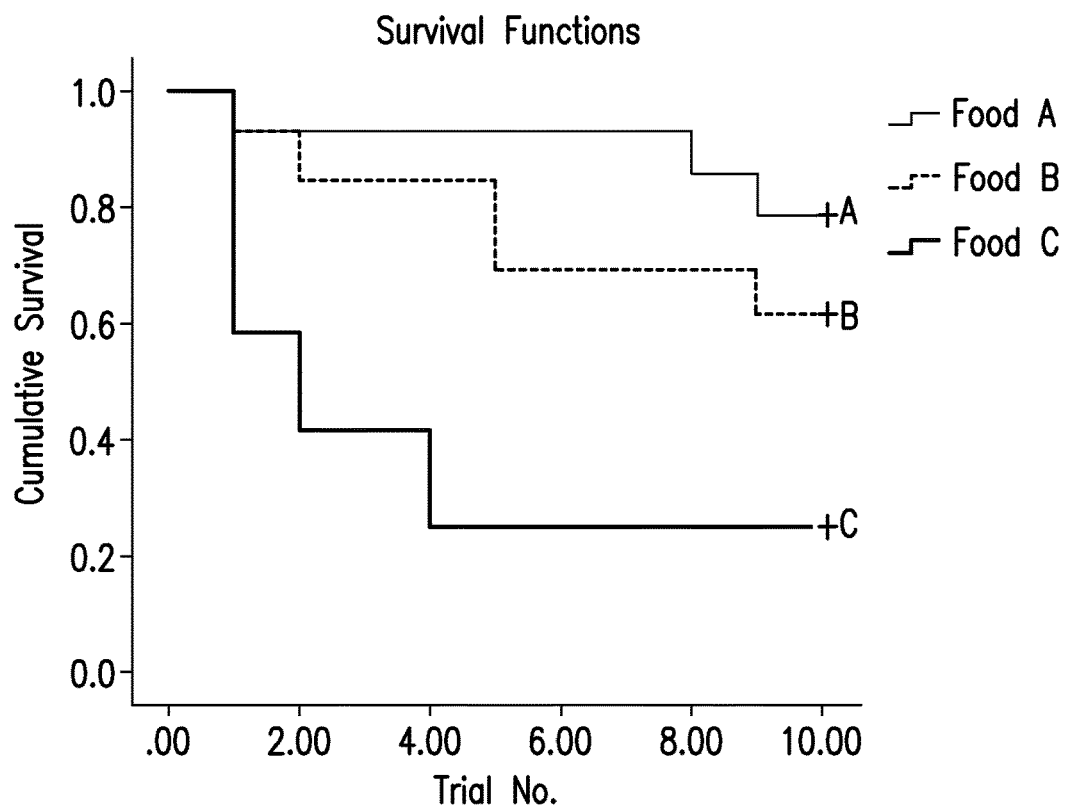
FIG. 6 depicts survival curves for the contrast studies in Example 1.

Each trial was conducted according a protocol presented to the simplified schematic diagram of FIG. 2. In each trial, a cat was presented with anticipatory cues lasting about 1 to 2 seconds. The anticipatory cues included an aural cue (shaking of the kibble in a plastic container) and a visual cue (showing the kibble and its plastic container). Food samples (2 pieces of kibble) were then presented to a subject cat in a bowl. The bowl was placed on the ground, in a position kept consistent throughout all trials with a given subject cat. Each cat in each trial was given a set presentation period ($t1$) of 30 seconds to explore the bowl containing the food sample. Each cat had an opportunity to eat the food sample or refuse the food sample within the presentation period. Any uneaten food was then removed. The bowl was left on the floor. Trials were then repeated as necessary without an inter-trial period. Cats were recorded by three camcorders at different angles throughout all trials. Instances of refusal, measured as trials in which at least one of the two kibbles in each sample remained uneaten, were recorded. The results of the Anticipation studies are shown in FIG. 3. The results of the Contrast studies are shown in FIG. 4. In both FIGS. 3 and 4, trial number is shown along the x axis and the proportion of cats eating the food in each trial is shown along the y axis. Survival analysis was conducted on the recorded instances of refusal from both the Anticipation studies and Contrast studies. Survival curves for the Anticipation studies are shown in FIG. 5. Survival curves for the Contrast studies are shown in FIG. 6. In both FIGS. 5 and 6, trial number is shown along the x axis, and the y axis presents the proportion of cats refusing to eat a given food sample for the first time. FIGS. 5 and 6 indicate that Food C tended to be refused before Food B, and Food B tended to be refused before Food A, consistent with Food A being the most palatable and Food C the least.

Figure 7:
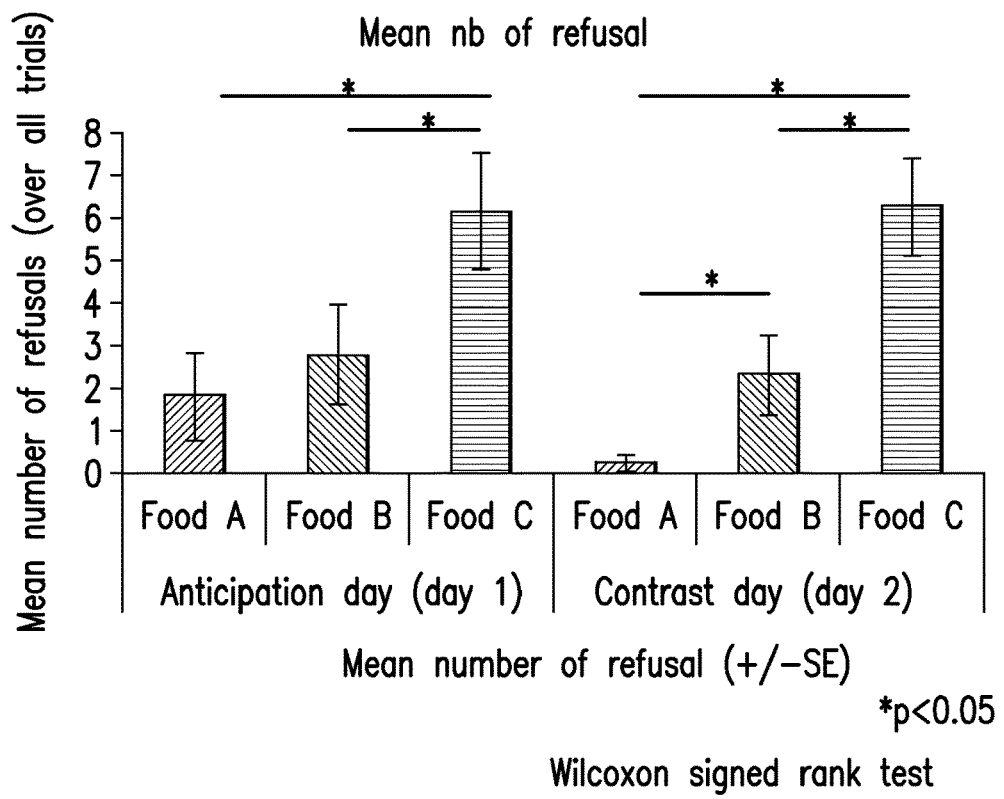
FIG. 7 presents mean refusals across the anticipation and contrast studies in Example 1.

Both the Anticipation and Contrast studies show that Food A was preferred to Food B, and Food B was preferred to Food C, in line with expectation. The study results are summarized in Table 2 and FIG. 7. In FIG. 7, the y axis presents the mean number of times each food was refused, over all trials. There were fewest instances of refusal with Food A and most instances of refusal with Food C. These studies established the cats' preference for Food A over Food B, and for Food B over Food C. These studies established that Food A had the highest palatability and Food C the lowest. Refusal tended to occur both earlier and more often for Food C than for Food B, and for Food B than for Food A.

TABLE 2

|  |  | Food A (High) | Food B (Med) | Food C (Low) |
| --- | --- | --- | --- | --- |
| Percentage of refusal | Anticipation day (Day 1) | 12% | 19% | 41% |
|  | Contrast day (Day 2) | 2% | 15% | 42% |

Refusal behavior tended to appear more quickly in cats that had been presented with high value tuna before being presented with the test food. FIG. 7 indicates that the test method was more sensitive when a high value contrast food was used ("Contrast day (day 2)") than when a high value contrast food was not used ("Anticipation day (day 1)"). As described above, this can be because the high value tuna built an expectation in the cats. Cats expecting high value tuna can show a heightened sensitivity to food palatability and food preference. In this way, use of a high value contrast food can increase the sensitivity of the presently disclosed methods.

As shown in FIG. 7, statistically meaningful differences in numbers of instances of refusal and statistically meaningful differences in cat food preference were measured even with a group of cats (14 cats) that was relatively small compared to group sizes used with existing methods. Data was analyzed using the Wilcoxon signed rank test with significance defined at the 5% level.

Example 2

Refusal-Based Testing with Trained Cattery Cats 2.1 Methods

Test room. Equipment and food boxes were ready in the test room. Prior to the cats being brought into the testing room, they were acclimated to the test room, which is a standard social housing room for cats at cattery. The test room included platforms, bedding and hiding boxes, one litter box and an automatic water bowl.

Feeding procedures. Presentations 1-5

Each cat was given five successive trials in a row (5 pieces) with the test food, with no time interval between presentations (no inter-trial period). All 5 presentations were completed by the handler (study administrator), even if a cat refused all or part of the diet offered.

Presentations 6-10

In the same way, 5 small pieces of tuna were given to each cat. All 5 presentations were completed by the handler, even if a cat refused all or part of the diet offered. Once again the pieces of food were given successively without any time interval.

Presentations 11-30

A small food box containing samples of the dry test food was shaken to provide a visual and audible (aural) anticipatory cue for 1-2 seconds, following a 30 second period in which one kibble was placed in a bowl.

A further 30 second period was then measured during which time a cat could either eat or refuse the food offered. At the end of the 30 second period, the diet was removed if it had not already been consumed. If a cat had eaten the food, it was recorded as 1 and, if not, a 0.

This procedure was then repeated to total 20 presentations.

The feeding procedure outlined above was repeated five times, for five distinct repetitions of the study (to confirm reproducibility).

Animals. 23 or 24 healthy domestic shorthair cats were involved in each repetition. All cats were familiarized with the handler prior to the study. The subject numbers, colors, ages, and groups of the cats studied are presented in Table 3.

TABLE 3

| Subject Number | Color | Age | Group |
|---|---|---|---|
| 1 | Grey Abby | 4.0 | 1 |
| 2 | Grey Abby | 4.0 | 1 |
| 3 | Grey Abby | 4.0 | 1 |
| 4 | Grey Mackerel Tabby & White | 4.0 | 1 |
| 5 | Blue Torti & White | 4.0 | 1 |
| 6 | Mackerel Tabby & White | 4.0 | 1 |
| 7 | Tabby | 3.7 | 1 |
| 8 | Abby & White | 3.5 | 1 |
| 9 | Tabby & White | 3.5 | 1 |
| 10 | Abby & White | 3.5 | 1 |
| 11 | Abby | 4.0 | 1 |
| 12 | Tabby & White | 4.0 | 1 |
| 13 | Tabby & White | 3.5 | 1 |
| 14 | Tabby | 2.7 | 1 |
| 15 | Ginger Mackerel Tabby & White | 1.0 | 2 |
| 16 | Tabby | 1.0 | 2 |
| 17 | Gray Tabby & White | 1.0 | 2 |
| 18 | Tabby & White | 1.0 | 2 |
| 19 | Mackerel Tabby | 1.0 | 2 |
| 20 | Mackerel Tabby & White | 1.0 | 2 |
| 21 | Tabby & White | 1.0 | 2 |
| 22 | Mackerel Tabby | 1.0 | 2 |
| 23 | Tabby Torti | 1.0 | 2 |
| 24 | Tabby | 1.0 | 2 |

Diets. Different types of dry food were used for the study: an uncoated monokibble (Food C), a tuna-flavored kibble (Food W), and a cat treat formulated to have relatively high palatability (Food D) as test foods. Tuna was used at the contrast food (high value) food.

Regular meals consisted of a chicken-flavored kibble (dry) and wet rotation diets, with energy intake split evenly between morning and afternoon feeds. The quantities fed were adapted daily to take into account the food received during testing. Prior to the study, every cat experienced all the different food products.

Data recorded. For each food sample presentation, the acceptance or refusal was recorded; for each repetition the average of refusal/acceptance and the index "last kibble accepted/acceptance" was calculated for each food (diet).

Statistical analyses. The analysis was fit with a binomial generalized linear mixed model, modelling the log odds of refusal against food, presentation order and their interaction as the fixed effects and cat as a random effect. Between diet contrasts were applied at each of the 5 presentations after the final tuna presentation.

2.2 Results

Figure 8:
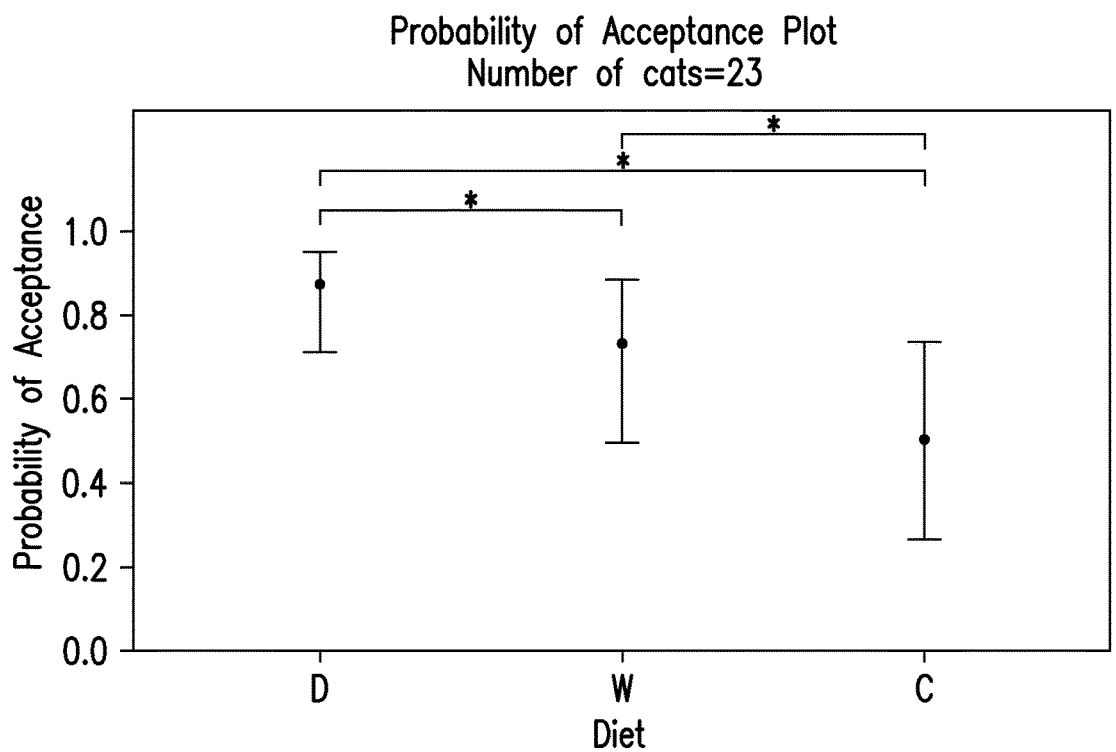
FIG. 8 provides probability of acceptance of food samples in the first trial in Example 2.
Figure 9:
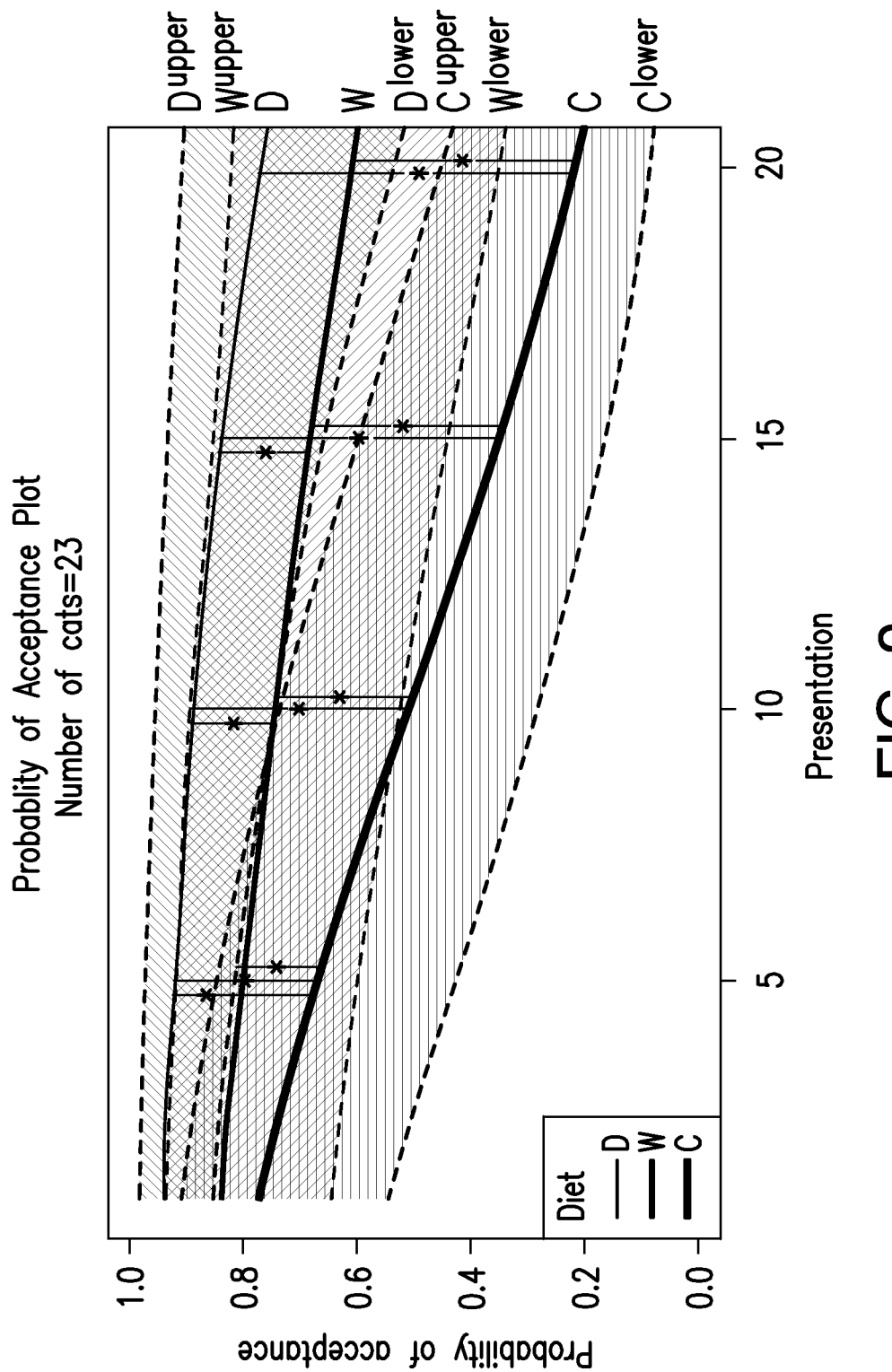
FIG. 9 depicts refusal rate of food samples in the first trial in Example 2.

First set of trials. The panel of cats showed different acceptance rates for each of the three foods: higher acceptance of the cat treat compared to tuna-flavored kibble and uncoated monokibble (FIGS. 8 and 9). FIG. 8 shows the probability of acceptance over all presentations for each food (cat treat=D, tuna-flavored kibble=W, uncoated monokibble=C), with a 95% confidence interval and *denoting statistical differences (at 5% level). FIG. 9 shows the refusal rate for each of the three tested foods; statistical comparisons were made at 5, 10, 15, and 20 presentations. In FIG. 9, probability of acceptance is represented with confidence interval. All significant differences (at each comparison point) are indicated with *; p<0.05. The difference between each of the diets was not found for all the comparison presentations (e.g. D vs W at comparison presentation 20).

Figure 10:
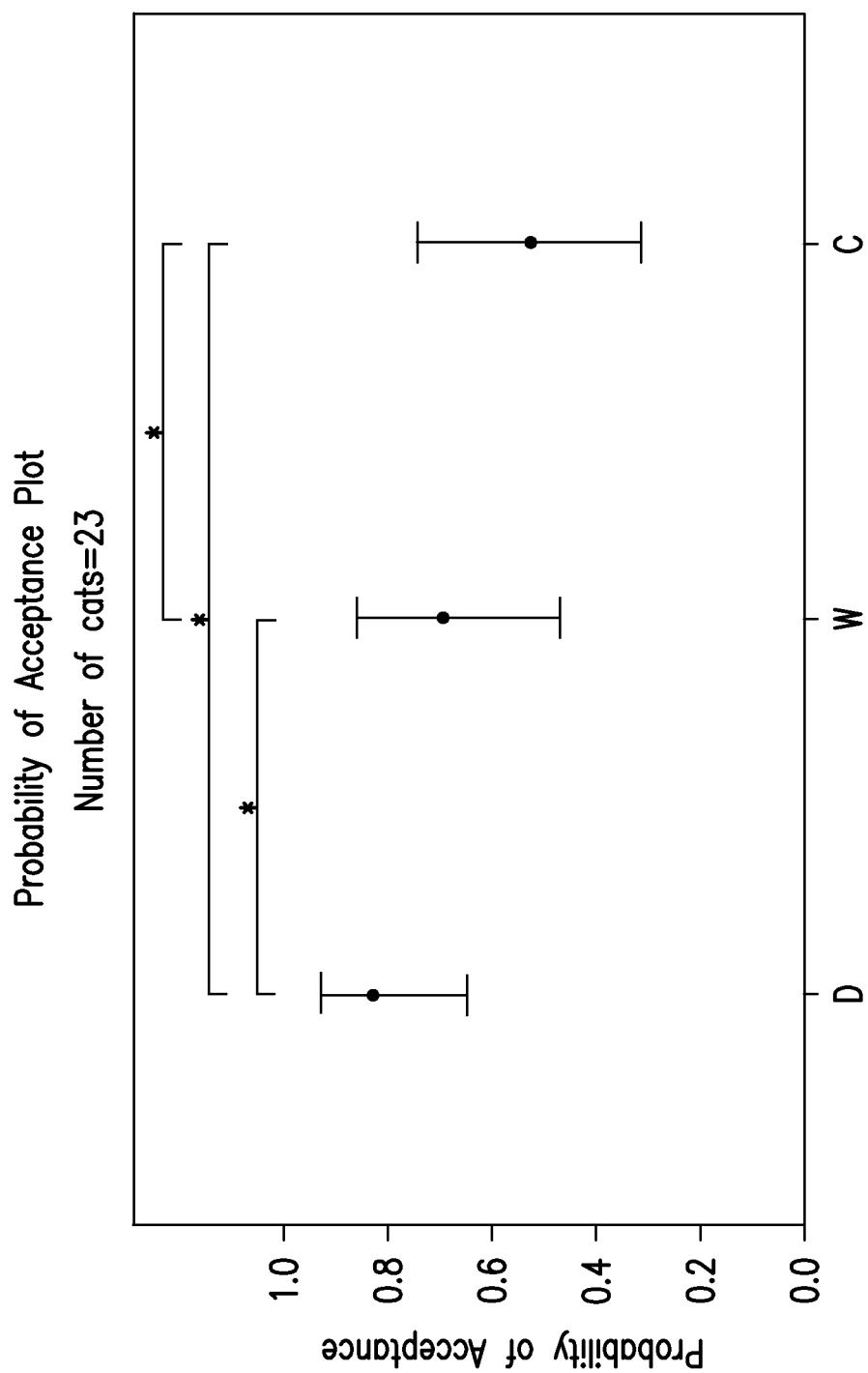
FIG. 10 provides probability of acceptance of food samples in the second trial in Example 2.
Figure 11:
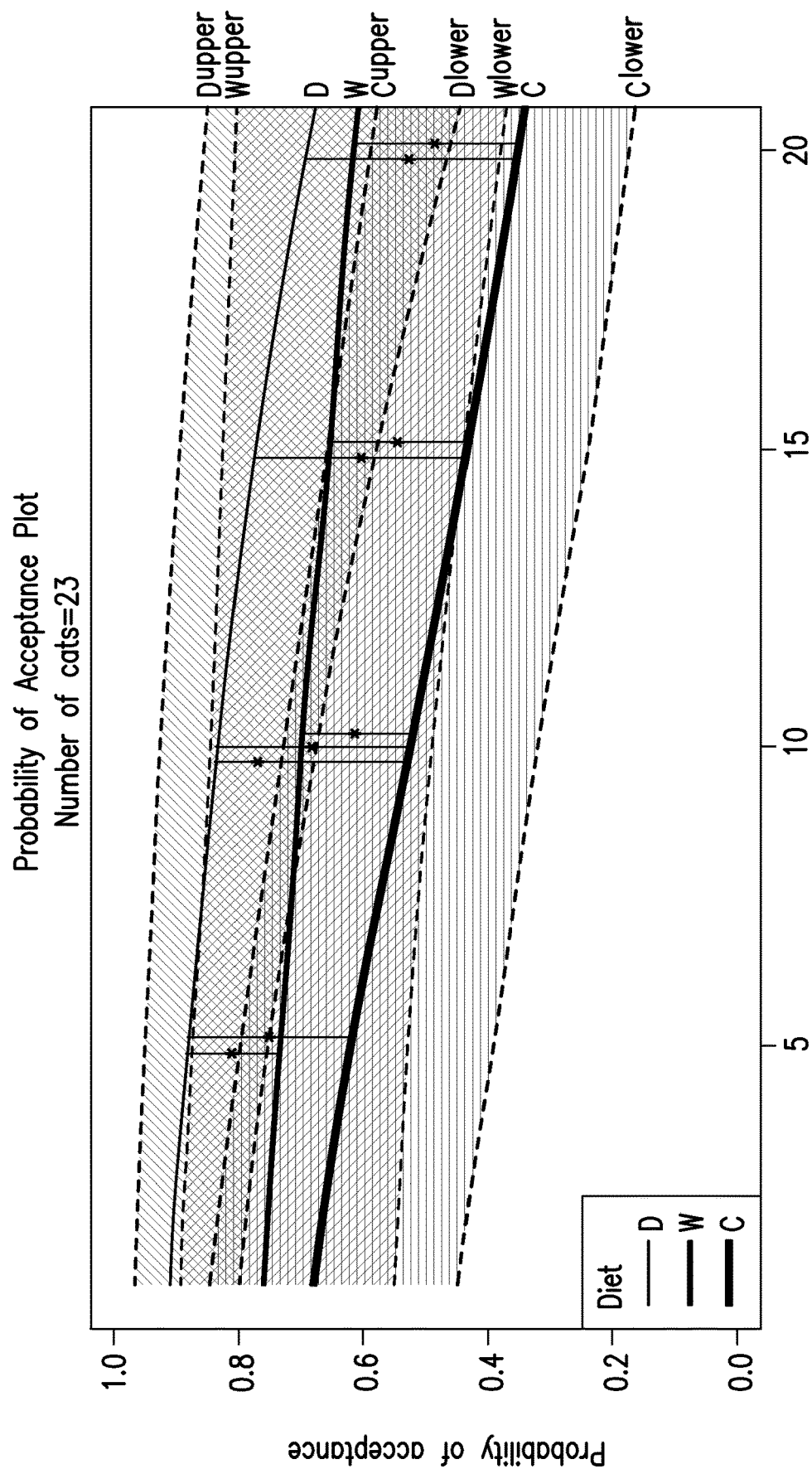
FIG. 11 depicts refusal rate of food samples in the second trial in Example 2.

Second repetition of trials. On second repetition, the panel of cats showed different acceptance rates for each of the three foods and the same trend as the first repetition: preference for the cat treat (D) compared to the tuna-flavored kibble (W) and uncoated monokibble (C) (FIGS. 10 and 11). FIG. 10 shows the probability of acceptance over all presentations for each food (cat treat=D, tuna-flavored kibble=W, uncoated monokibble=C), with a 95% confidence interval and*denoting statistical differences (at 5% level). FIG. 11 shows the refusal rate for each of the three tested foods; statistical comparisons were made at 5, 10, 15, and 20 presentations. In FIG. 11, probability of acceptance is represented with confidence interval. All significant differences (at each comparison point) are indicated with*; $p<0.05$. At presentation point 10, a significant difference was found between each of the three foods.

Figure 12:
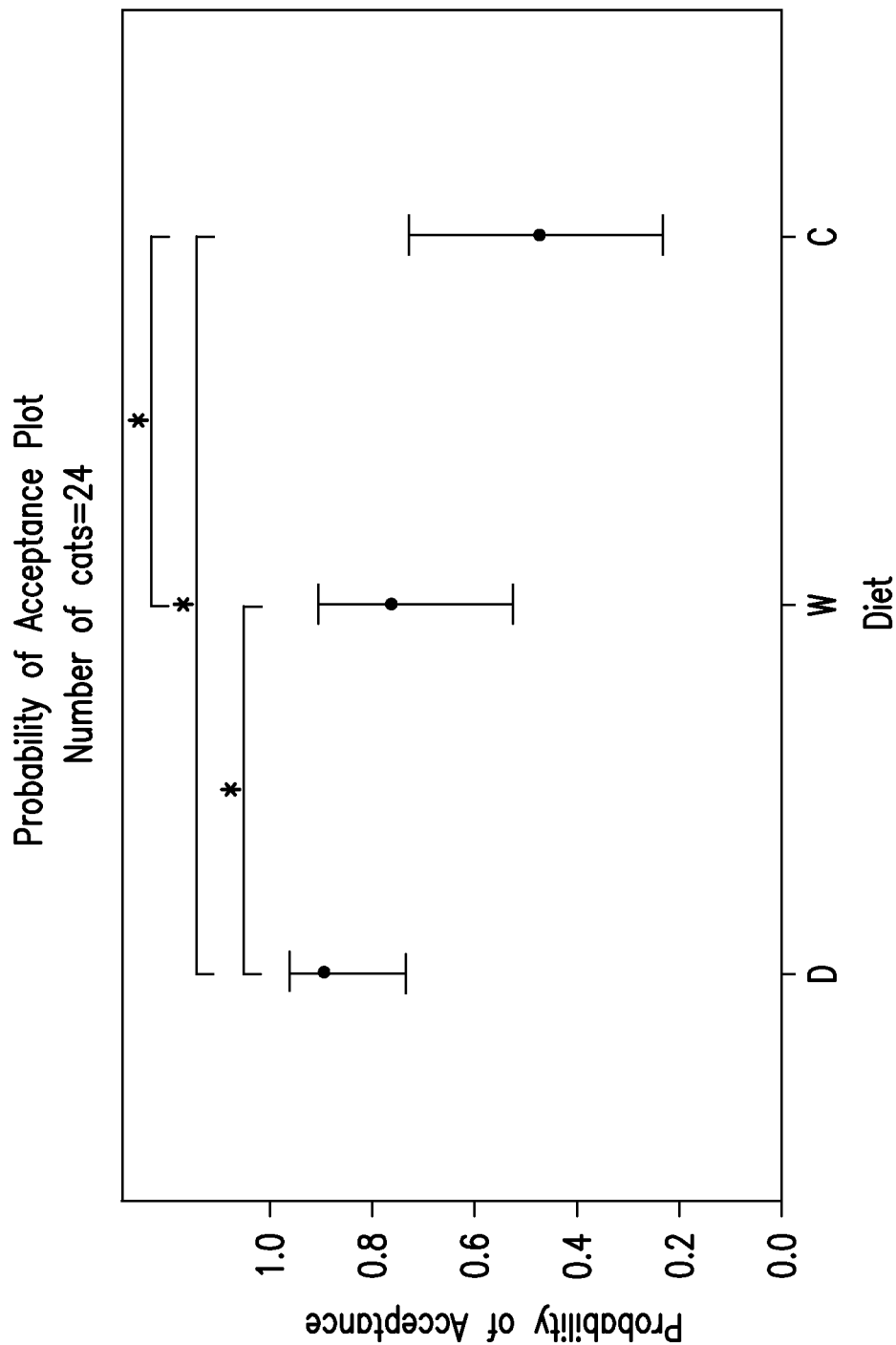
FIG. 12 provides probability of acceptance of food samples in the third trial in Example 2.
Figure 13:
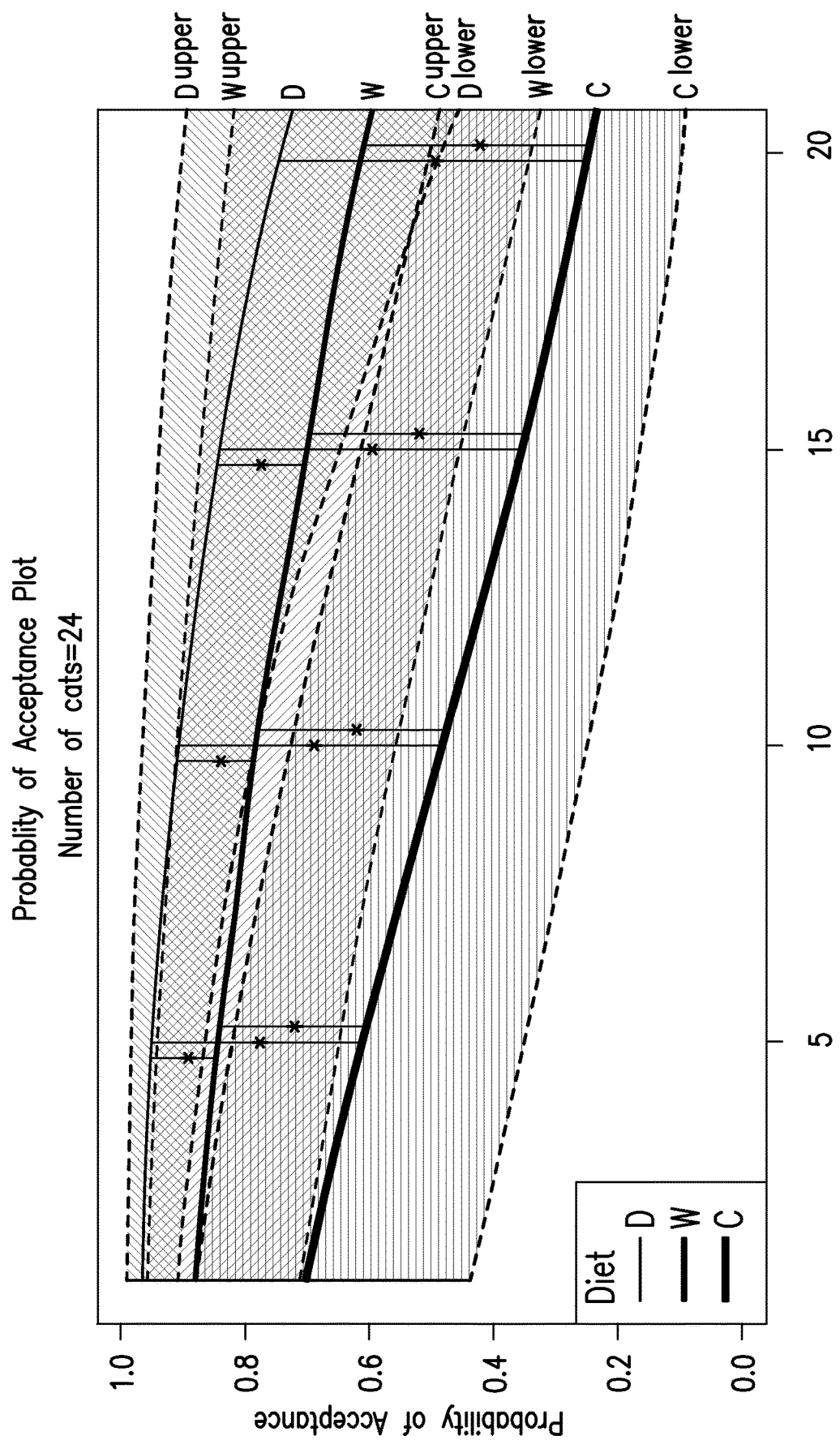
FIG. 13 depicts refusal rate of food samples in the third trial in Example 2.

Third repetition of trials. On third repetition, the panel of cats showed different acceptance rates for each of the three foods and the same trend as the first and second repetitions: preference for the cat treat (D) compared to the tuna-flavored kibble (W) and uncoated monokibble (C) (FIGS. 12 and 13). FIG. 12 shows the probability of acceptance over all presentations for each food (cat treat=D, tuna-flavored kibble=W, uncoated monokibble=C), with a 95% confidence interval and*denoting statistical differences (at 5% level). FIG. 13 shows the refusal rate for each of the three tested foods; statistical comparisons were made at 5, 10, 15, and 20 presentations. In FIG. 13, probability of acceptance is represented with confidence interval. All significant differences (at each comparison point) are indicated with *; $p<0.05$.

Figure 14:
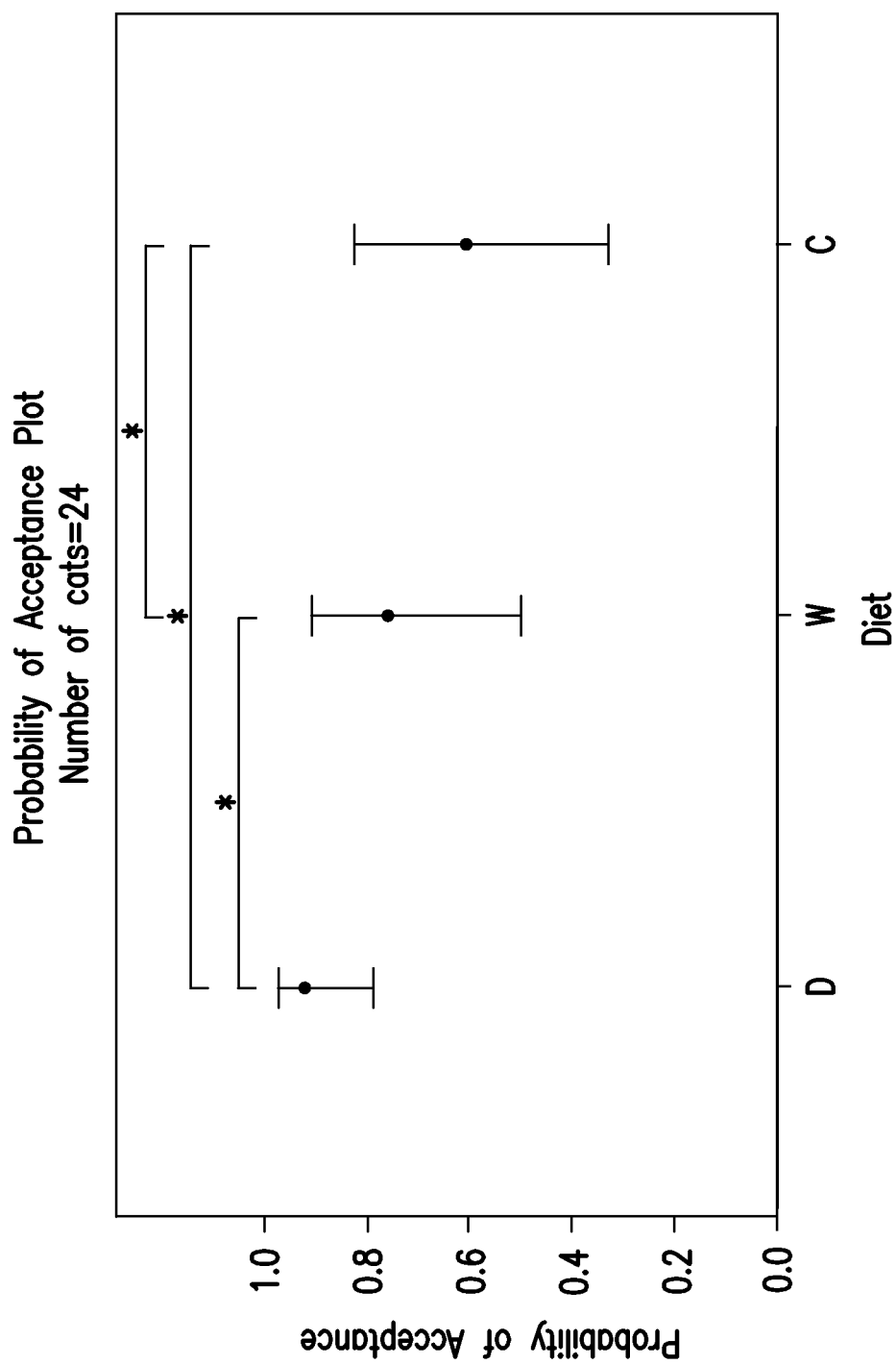
FIG. 14 provides probability of acceptance of food samples in the fourth trial in Example 2.
Figure 15:
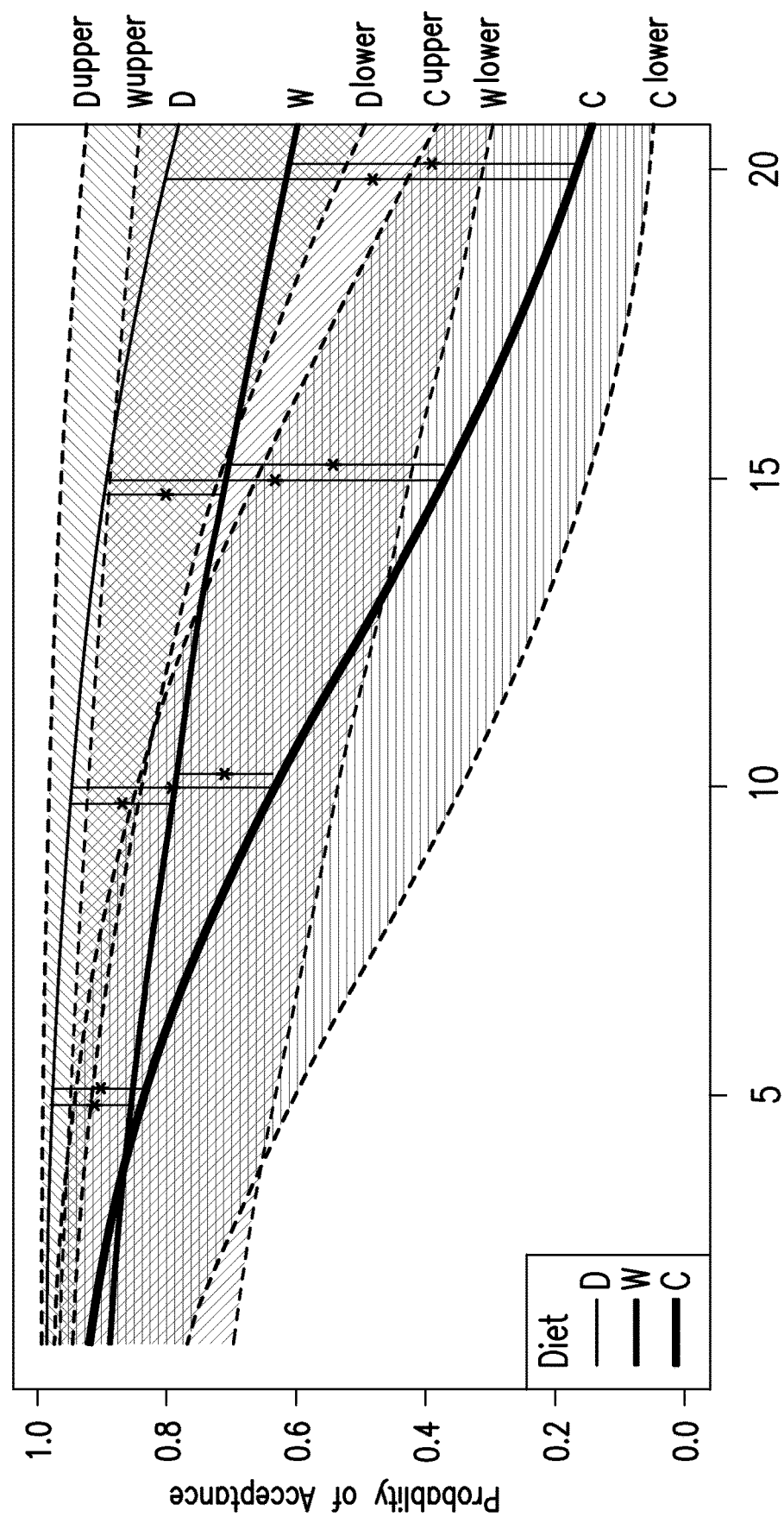
FIG. 15 depicts refusal rate of food samples in the fourth trial in Example 2.

Fourth repetition of trials. On fourth repetition, the panel of cats showed different acceptance rates for each of the three foods and the same trend as the first and second repetitions: preference for the cat treat (D) compared to the tuna-flavored kibble (W) and uncoated monokibble (C) (FIGS. 14 and 15). FIG. 14 shows the probability of acceptance over all presentations for each food (cat treat=D, tuna-flavored kibble=W, uncoated monokibble=C), with a 95% confidence interval and*denoting statistical differences (at 5% level). FIG. 15 shows the refusal rate for each of the three tested foods; statistical comparisons were made at 5, 10, 15, and 20 presentations. In FIG. 15, probability of acceptance is represented with confidence interval. All significant differences (at each comparison point) are indicated with*; $p<0.05$.

Figure 16:
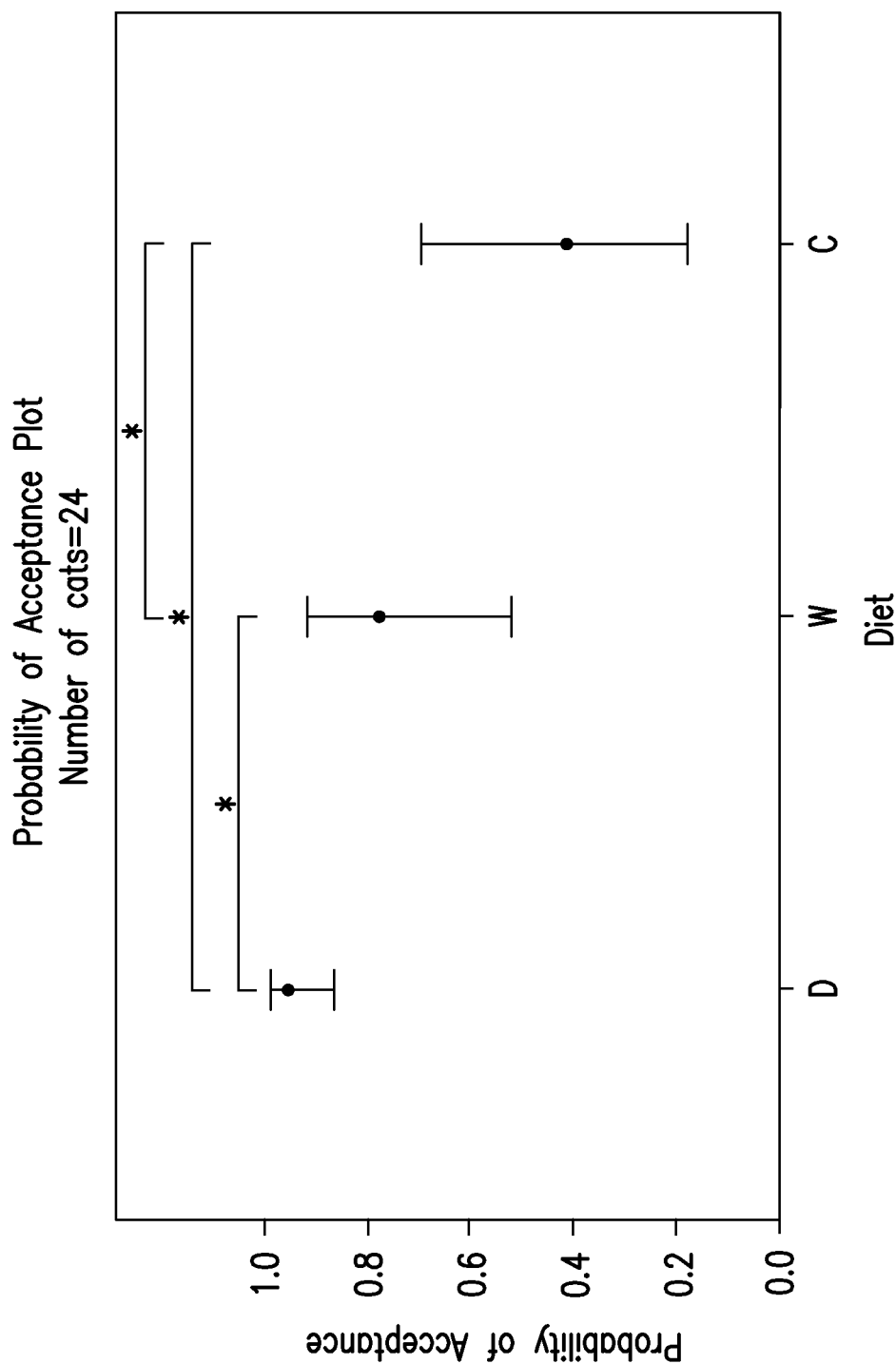
FIG. 16 provides probability of acceptance of food samples in the fifth trial in Example 2.
Figure 17:
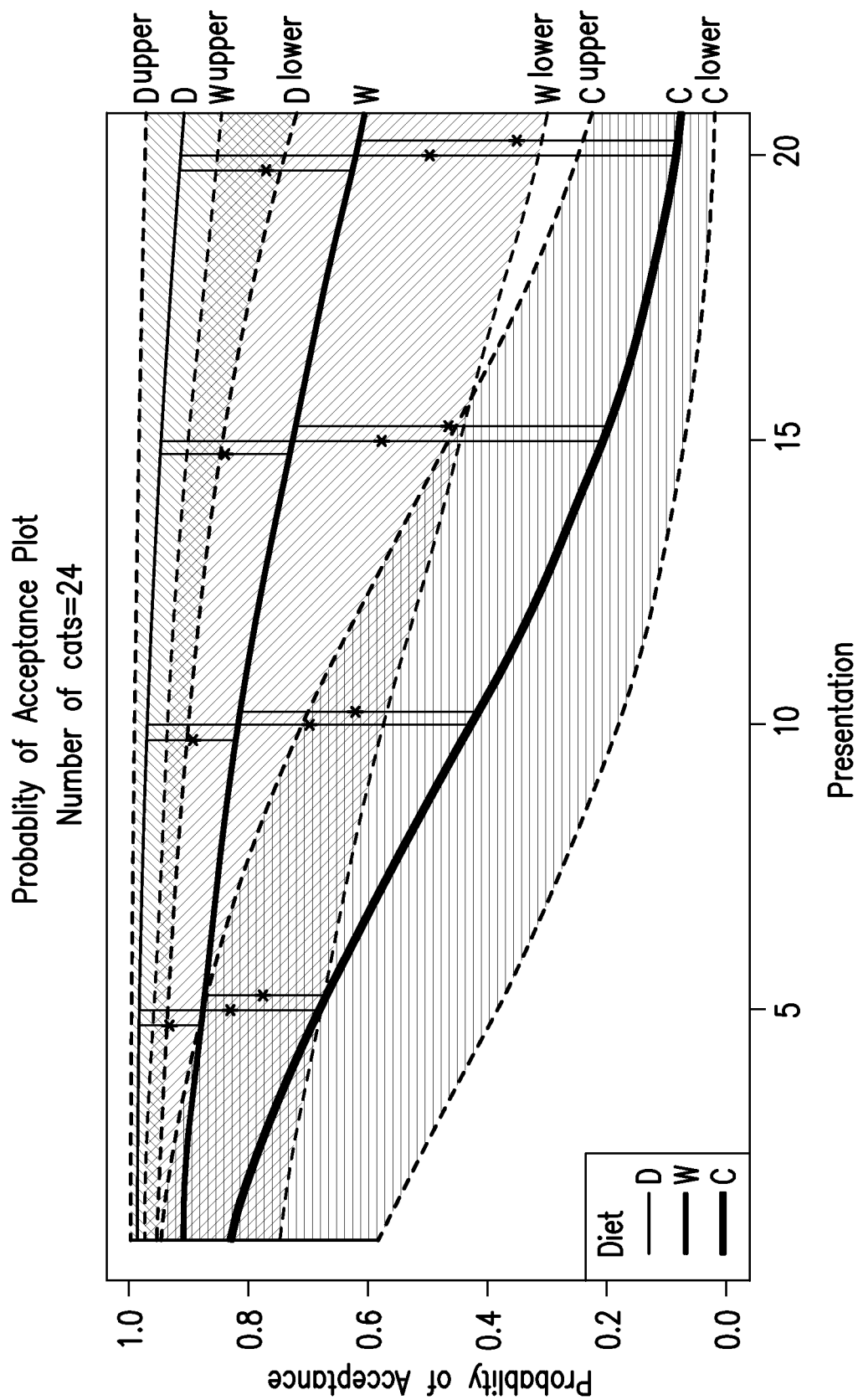
FIG. 17 depicts refusal rate of food samples in the fifth trial in Example 2.

Fifth repetition of trials. On fifth repetition, the panel of cats showed different acceptance rates for each of the three foods and the same trend as the first and second repetitions: preference for the cat treat (D) compared to the tuna-flavored kibble (W) and uncoated monokibble (C) (FIGS. 16 and 17). FIG. 16 shows the probability of acceptance over all presentations for each food (cat treat=D, tuna-flavored kibble=W, uncoated monokibble=C), with a 95% confidence interval and*denoting statistical differences (at 5% level). FIG. 17 shows the refusal rate for each of the three tested foods; statistical comparisons were made at 5, 10, 15, and 20 presentations. In FIG. 17, probability of acceptance is represented with confidence interval. All significant differences (at each comparison point) are indicated with*; $p<0.05$. As shown in FIG. 17, in the fifth repetition of the trials, significant differences were found at each comparison point.

Figure 18:
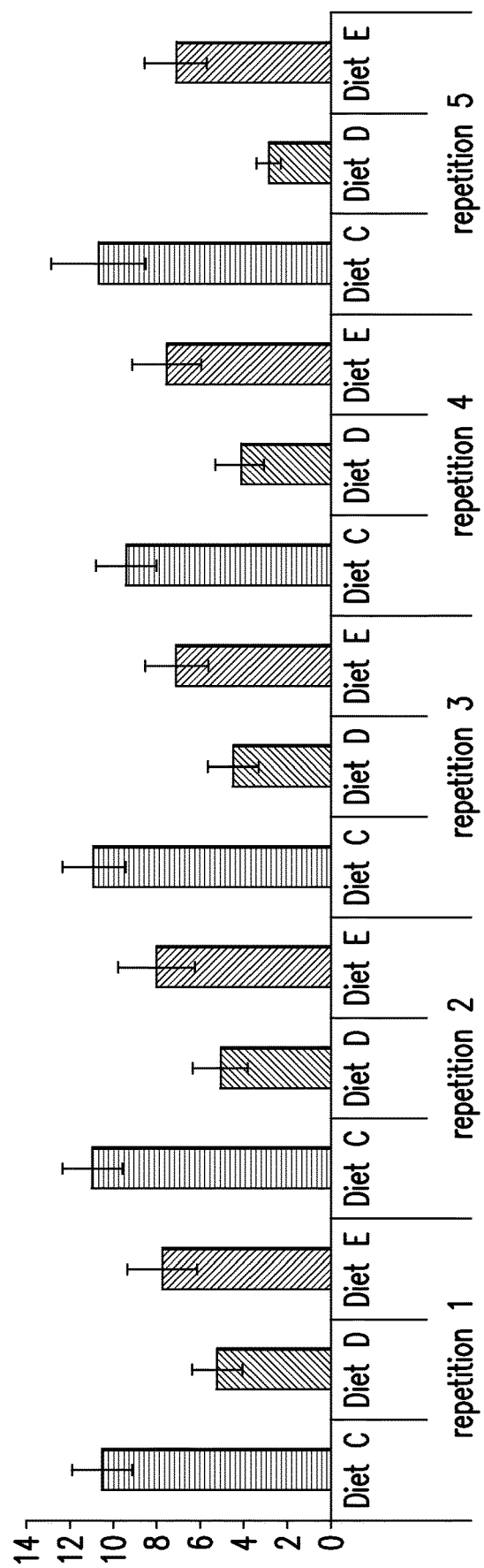
FIG. 18 presents mean refusal for foods in each repetition of trials described in Example 2.

General comparison. Across the five repetitions, the cat panelists ranked the three different food products in the same order and showed similar refusal rates across the five repetitions (repeated studies) (FIG. 18). FIG. 18 shows mean refusal (+/−standard error) for each food in each repetition of the trials. Diet C (Food C) is the uncoated monokibble. Diet D (Food D) is the cat treat. Diet E (Food E, also denoted Food W) is the tuna-flavored kibble.

Figure 19:
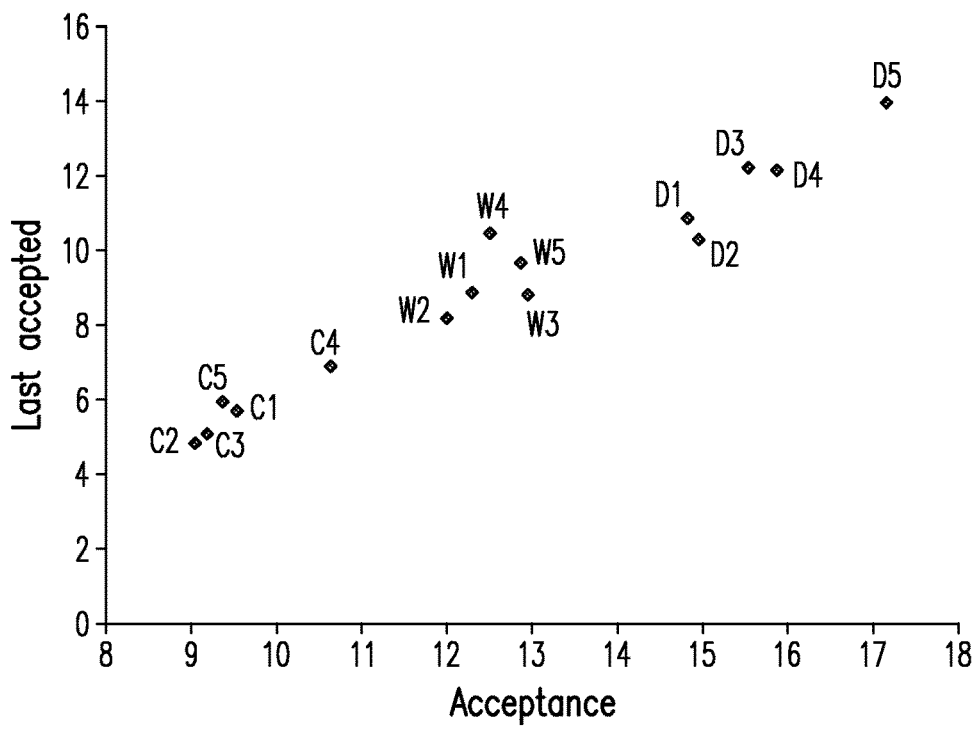
FIG. 19 provides the average computed value for last kibble accepted over the average computed value for first refusal as described in Example 2.

For each food, an Index was reported on a two dimensional graph: the average computed value for last kibble accepted ("Last accepted," y axis) and the average computed value for first refusal ("Acceptance," x axis) in order to characterize both the motivation/distractibility of the cat and its food acceptance (FIG. 19). In the data points of FIG. 19, the letters refer to the food tested (D=cat treat, W=tuna-flavored kibble, C=uncoated monokibble) and numbers (1 to 5) to the repetition.

2.3 Discussion

Based on the refusal rate (or probability of acceptance) determined from the method described above, the cats differentiated between the three foods and ranked them in order of palatability and preference. The order of palatability and preference was as expected, with the cat treat the highest ranked followed by the tuna-flavored kibble, and uncoated kibble least preferred.

Even if the differences at each of the individual comparison points were not always significant, the average acceptance rate for a session was significant, and statistically significant differences in refusal/acceptance were found in at least one presentation point (number of trials) in each repetition (e.g., after 10 trials).

The cats ranked the foods in the same order in the five repetitions. The successive repetitions of the test with the same products did not appear to influence (in any direction) the probability of acceptance.

It is important to note that even the cat treat was not at the ceiling level of the test. That is, the cat treat was sometimes refused. This finding indicates there is space "above" the cat treat that very highly palatable cat foods could occupy.

Example 3

Refusal-Based Testing with Trained Kennel Dogs 3.1 Methods

Test room. Equipment and food boxes were ready in the test room. Prior to the dogs being brought into the testing room, they were acclimated to the test room, which is a standard social housing room for dogs at kennel. The test room included, bedding and water bowl.

Feeding procedures. Presentations 1-5

Each dog was given five successive trials in a row (5 pieces) with the test food, with no time interval between presentations (no inter-trial period). All 5 presentations were completed by the handler (study administrator), even if a dog refused all or part of the diet offered.

Presentations 6-10

In the same way, 5 small pieces of tuna were given to each dog. All 5 presentations were completed by the handler, even if a dog refused all or part of the diet offered. Once again the pieces of food were given successively without any time interval.

Presentations 11-30

A small food box containing samples of the dry test food was shaken to provide a visual and audible (aural) anticipatory cue for 1-2 seconds, following a 30 second period in which one kibble was placed in a bowl.

A further 30 second period was then measured during which time a dog could either eat or refuse the food offered. At the end of the 30 second period, the diet was removed if it had not already been consumed. If a dog had eaten the food, it was recorded as 1 and, if not, a 0.

This procedure was then repeated to total 20 presentations.

The feeding procedure outlined above was repeated two times, for two distinct repetitions of the study (to confirm reproducibility).

Animals. 9-10 healthy Yorkshire Terrier dogs were involved in each repetition. All dogs were familiarized with the handler prior to the study. The names, sex, breed, ages, and groups of the dogs studied are presented in Table 4.

TABLE 4

| Dog Name | Sex | Breed | Age | Group |
|---|---|---|---|---|
| Radley | F | Yorkshire | 2.8 | 1 |
| Skittle | F | Yorkshire | 2.7 | 1 |
| Ulric | M | Yorkshire | 2.5 | 1 |
| Vixen | F | Yorkshire | 2.5 | 2 |
| Vienna | F | Yorkshire | 2.5 | 2 |
| Albert | M | Yorkshire | 1.8 | 2 |
| Charlton | M | Yorkshire | 1.5 | 1 |
| Cody | M | Yorkshire | 1.5 | 1 |
| Elmo | M | Yorkshire | 1 | 2 |
| Elf | M | Yorkshire | 1 | 2 |

Diets. Different types of commercially avalible dry food were used for the study: Diet A and Diet B. Tuna was used as the contrast food (high value) food.

Regular meals consisted of a chicken-flavored kibble (dry) and wet rotation diets, with energy intake split evenly between morning and afternoon feeds. The quantities fed were adapted daily to take into account the food received during testing. Prior to the study, every dog experienced all the different food products.

Data recorded. For each food sample presentation, the acceptance or refusal was recorded; for each repetition the average of refusal/acceptance was calculated for each food (diet).

Statistical analyses. The analysis was fit with a binomial generalized linear mixed model, modelling the log odds of refusal against food, presentation order and their interaction as the fixed effects and dog as a random effect. Between diet contrasts were applied at each 5 presentations after the final tuna presentation.

3.2 Results

Figure 20:
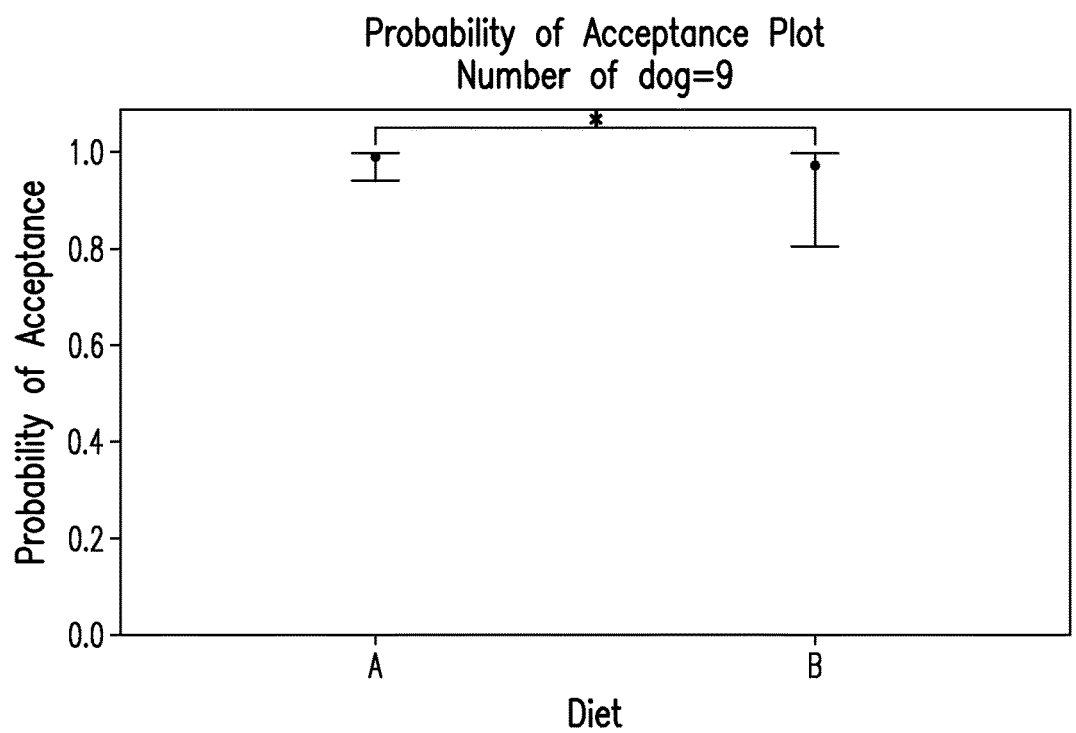
FIG. 20 provides the probability of acceptance of food as described in Example 3.
Figure 21:
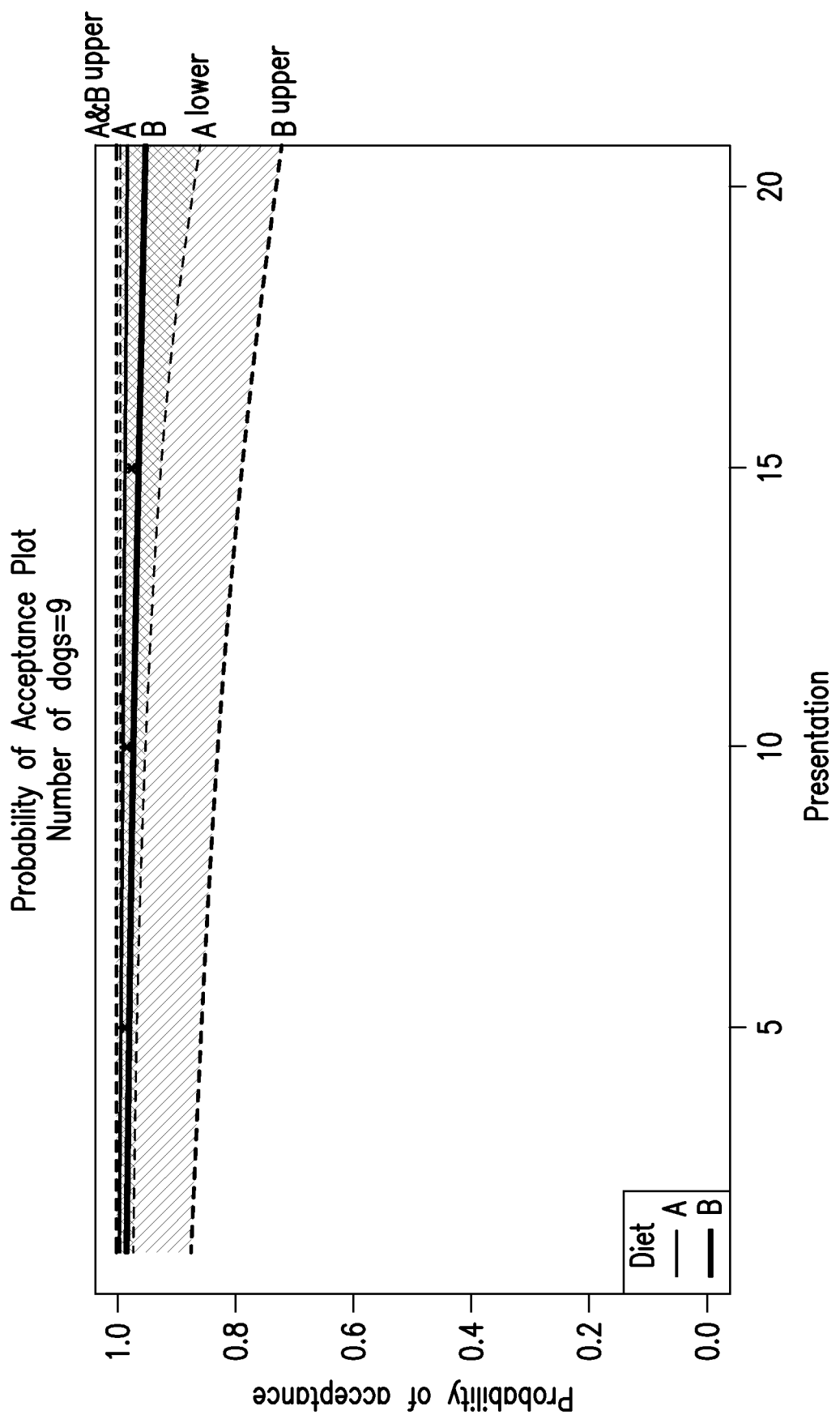
FIG. 21 shows the refusal rate for the foods tested Example 3.

Trials. The trials were performed with two trial repetitions on the panel of dogs, the results were then combined (FIG. 20, 21), the dogs showed different acceptance rates for each of the two foods: higher acceptance of Diet A compared to Diet B General comparison. Across the two repetitions, the dog panelists ranked the two different food products in the same order and showed similar mean refusal rates across the two repetitions (repeated studies) (FIG. 20,21). FIG. 20 shows the probability of acceptance over all presentations for each food. Diet A=A commercially available dry diet, Diet B=B commercially available dry diet, with a 95% confidence interval and*denoting statistical difference (at 5% level). FIG. 21 shows the refusal rate for each of the two tested food; statistical comparisons were made at 5, 10, 15 and 20 presentations. In FIG. 21, probability of acceptance is represented with confidence interval. All significant differences (at each comparison point) are indicated with *; $p<0.05$.

3.3 Discussion

Based on the refusal rate (or probability of acceptance) determined from the method described above, the dogs differentiated between the two foods and ranked them in order of palatability and preference. The order of palatability and preference was as expected, with the commercial diet A the highest ranked.

Even if the differences at each of the individual comparison points were not always significant, the average acceptance rate was significant, and statistically significant differences in refusal/acceptance were found in at least one presentation point (number of trials) in each repetition.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compounds and compositions of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of selecting a preferred cat or dog food, comprising performing the following steps in sequential order:
    (a) establishing a first baseline of food receptiveness, which comprises:
        1. presenting a first sample of a high value contrast food to a cat or dog;
        2. removing the first sample of the high value contrast food after a set duration of time, t1;
        3. recording first instances of refusal of the high value contrast food;
        4. optionally, repeating steps (1) through (3) one or more times; and
        5. computing a total number of first instances of refusal of the high value contrast food;
    (b) introducing a first test food, which comprises:
        6. presenting a sample of the first test food to the cat or dog;
        7. removing the sample of the first test food after the set duration of time, t1;
        8. recording instances of refusal of the first test food;
        9. optionally, repeating steps (6) through (8) one or more times; and
        10. computing a total number of instances of refusal of the first test food;
    (c) establishing a second baseline of food receptiveness, which comprises:
        11. presenting a second sample of the high value contrast food to the cat or dog;
        12. removing the second sample of the high value contrast food after the set duration of time, t1;
        13. recording second instances of refusal of the high value contrast food;
        14. optionally, repeating steps (11) through (13) one or more times; and
        15. computing a total number of second instances of refusal of the high value contrast food;
    (d) introducing a second test food different from the first test food, which comprises:
        16. presenting a sample of the second test food to the cat or dog;
        17. removing the sample of the second test food after the set duration of time, t1;

18. recording instances of refusal of the second test food;
19. optionally, repeating steps (16) through (18) one or more times; and
20. computing a total number of instances of refusal of the second test food; and
(e) selecting the preferred cat or dog food between the first test food and the second test food by comparing the total number of instances of refusal of the first test food and the total number of instances of refusal of the second test food and selecting the test food with a lower total number of instances of refusal;
wherein the high value contrast food has a different composition than either the first test food and the second test food and is palatable to the cat or the dog, and wherein t1 is between about 5 seconds and about 60 seconds.

2. A method of selecting a preferred cat or dog food, comprising performing the following steps in sequential order:
(a) establishing a baseline of food receptiveness to a first test food, which comprises:
1. presenting an initial sample of the first test food to an animal, wherein the animal is a cat or a dog;
2. removing the initial sample of the first test food after a set duration of time, t1;
3. recording initial instances of refusal of the first test food; and
4. optionally, repeating steps (1) through (3) one or more times;
(b) introducing a first disruption in food receptiveness, which comprises:
5. presenting a first sample of a high value contrast food to the animal;
6. removing the first sample of the high value contrast food after the set duration of time, t1;
7. recording first disruption instances of refusal of the high value contrast food;
8. optionally, repeating steps (5) through (7) one or more times; and
9. computing a total number of initial instances of refusal of the high value contrast food;
(c) reintroducing the first test food to the animal, which comprises:
10. presenting a subsequent sample of the first test food to the animal;
11. removing the subsequent sample of the first test food after the set duration of time, t1;
12. recording reintroduced instances of refusal of the first test food;
13. optionally, repeating steps (10) through (12) one or more times; and
14. computing a total number of instances of refusal of the first test food by adding the initial instances of refusal of the first test food and the reintroduced instances of refusal of the first test food;
(d) establishing a baseline of food receptiveness to a second test food different from the first test food, which comprises;
15. presenting an initial sample of the second test food to the animal;
16. removing the initial sample of the second test food after the set duration of time, t1;
17. recording initial instances of refusal of the second test food;
18. optionally, repeating steps (15) through (17) one or more times;
(e) introducing a second disruption in food receptiveness, which comprises:
19. presenting a second sample of the high value contrast food to the animal;
20. removing the second sample of the high value contrast food after the set duration of time, t1;
21. recording second disruption instances of refusal of the high value contrast food;
22. optionally, repeating steps (19) through (21) one or more times; and
23. computing a total number of second instances of refusal of the high value contrast food;
(f) reintroducing the second test food to the animal, which comprises:
19. presenting a subsequent sample of the second test food to the animal;
20. removing the subsequent sample of the second test food after the set duration of time, t1;
21. recording subsequent instances of refusal of the second test food;
22. optionally, repeating steps (24) through (26) one or more times; and
23. computing a total number of instances of refusal of the second test food by adding the initial instances of refusal of the second test food and the subsequent instances of refusal of the second test food; and
(g) selecting the preferred cat or dog food by comparing the total number of instances of refusal of the first test food and the total number of instances of refusal of the second test food and selecting the test food with a lower total number of instances of refusal;
wherein the high value contrast food has a different composition than either the first test food and the second test food and is palatable to the animal, and wherein t1 is between about 5 seconds and about 60 seconds.

3. The method of claim 2, wherein the animal is an untrained house cat or dog.

4. The method of claim 2, further comprising presenting the animal with one or more anticipatory cues that signal feeding prior to presenting the initial or subsequent sample of the first test food and/or the initial or subsequent sample of the second test food to the animal.

5. The method of claim 2, wherein all steps are performed within one day.

6. The method of claim 2, wherein the method is automated.

7. The method of claim 2, wherein each of the first test food and the second test food is independently selected from the group consisting of dry cat or dog foods, wet cat or dog foods, cat or dog treats, cat or dog care products, raw materials for dry cat or dog foods, raw materials for wet cat or dog foods, and combinations thereof.

8. The method of claim 2, wherein the animal is satiated prior to performing the method, as evidenced by a lack of expression of appetite or desire.

9. The method of claim 8, wherein the animal is fed about 50% of their metabolic energy requirement prior to performing the method.

10. The method of claim 8, wherein the animal is fed a standard meal prior to performing the method.

11. The method of claim 2, wherein each of the recording initial instances of refusal of the first test food, the recording first disruption instances of refusal of the high value contrast food, the recording reintroduced instances of refusal of the first test food, the recording initial instances of refusal of the second test food, the recording second disruption instances of refusal of the high value contrast food, and the recording subsequent instances of refusal of the second test food is independently selected from the group consisting of: recording refusal to approach a food sample, recording refusal to begin eating a food sample, recording refusal to finish eating a food sample, and combinations thereof.

12. A method of testing a cat or dog food, comprising:
preparing a first cat or dog food from at least one of fish, poultry, meat, dairy products, grains, vegetables, and combinations thereof; and
determining a relative palatability of the first cat or dog food;
wherein determining the relative palatability of the first cat or dog food comprises performing the following steps in sequential order:
(a) establishing a baseline of food receptiveness to the first cat or dog food by presenting an initial first sample to a first animal, the first animal being one of a cat or a dog, removing the initial first sample after a set duration of time, t1, and recording instances of refusal of the initial first sample, wherein t1 is between about 5 seconds and about 60 seconds;
(b) introducing a first disruption in food receptiveness by presenting an initial contrast sample of a contrast food to the first animal, removing the initial contrast sample after the set duration of time, t1, and recording first disruption instances of refusal of the initial contrast sample;
(c) reintroducing the first cat or dog food to the first animal by presenting a subsequent first sample of the first test food to the first animal, removing the subsequent first sample after the set duration of time, t1, and recording instances of refusal of the subsequent first sample;
(d) establishing a baseline of food receptiveness to a second cat or dog food by presenting an initial second sample to a second animal, the second animal being one of a cat or a dog, removing the initial second sample after the set duration of time, t1, and recording instances of refusal of the initial second sample;
(e) introducing a second disruption in food receptiveness by presenting a subsequent contrast sample of the contrast food to the second animal, removing the subsequent contrast sample after the set duration of time, t1, and recording second disruption instances of refusal of the subsequent contrast sample;
(f) reintroducing the second cat or dog food to the second animal by presenting a subsequent second sample of the second test food to the second animal, removing the subsequent second sample after the set duration of time, t1, and recording instances of refusal of the subsequent second sample; and
(g) calculating the relative palatability of the first cat or dog food by comparing a computed total number of instances of refusal of the initial and subsequent first samples with a computed total number of instances of refusal of the initial and subsequent second samples.

* * * * *